(12) United States Patent
Brooks et al.

(10) Patent No.: US 8,430,894 B2
(45) Date of Patent: Apr. 30, 2013

(54) FLOATING GASTROINTESTINAL ANCHOR

(75) Inventors: Jeffrey S. Brooks, Ra'anana (IL); Eran Hirszowicz, Ramat Gan (IL)

(73) Assignee: Spatz-Fgia, Inc., Great Neck, NY (US)

( * ) Notice: Subject to any disclaimer, the term of this patent is extended or adjusted under 35 U.S.C. 154(b) by 662 days.

(21) Appl. No.: 11/718,795

(22) PCT Filed: Mar. 28, 2007

(86) PCT No.: PCT/IL2007/000398
§ 371 (c)(1),
(2), (4) Date: Jul. 9, 2007

(87) PCT Pub. No.: WO2007/110866
PCT Pub. Date: Oct. 4, 2007

(65) Prior Publication Data
US 2009/0287231 A1 Nov. 19, 2009

Related U.S. Application Data

(60) Provisional application No. 60/787,124, filed on Mar. 28, 2006, provisional application No. 60/815,624, filed on Jun. 21, 2006.

(51) Int. Cl.
*A61B 17/08* (2006.01)
(52) U.S. Cl.
USPC .......... 606/151; 606/153; 606/157; 606/191; 606/192
(58) Field of Classification Search .............. 606/153, 606/191, 151, 157, 192, 193
See application file for complete search history.

(56) References Cited

U.S. PATENT DOCUMENTS

| | | | |
|---|---|---|---|
| 4,102,342 A | 7/1978 | Akiyama et al. |
| 4,315,509 A | 2/1982 | Smit |
| 4,416,267 A | 11/1983 | Garren et al. |
| 4,447,227 A | 5/1984 | Kotsanis |
| 4,485,805 A | 12/1984 | Foster, Jr. |
| 4,598,699 A | 7/1986 | Garren et al. |
| 4,694,827 A | 9/1987 | Weiner et al. |
| 4,696,288 A | 9/1987 | Kuzmak et al. |

(Continued)

FOREIGN PATENT DOCUMENTS

| | | |
|---|---|---|
| CA | 1233387 | 3/1988 |
| CA | 2068715 | 2/1992 |

(Continued)

OTHER PUBLICATIONS

U.S. Appl. No. 60/787,124.

(Continued)

*Primary Examiner* — Gary Jackson
*Assistant Examiner* — Kevin Everage
(74) *Attorney, Agent, or Firm* — Venable LLP; Michael V. Frank

(57) ABSTRACT

Apparatus (90) is provided for use in a stomach of a subject. The apparatus includes a balloon (92), adapted for placement in the stomach, and all anchor (102), coupled to the balloon. The anchor is adapted to prevent the balloon from passing into a duodenum of the subject. The apparatus further includes an inflation tube (96), coupled to the balloon to permit inflation of the balloon, and is adapted to stretch from the stomach to a mouth of the subject to facilitate inflation of the balloon. Other embodiments are also described.

50 Claims, 20 Drawing Sheets

U.S. PATENT DOCUMENTS

| | | | |
|---|---|---|---|
| 4,738,667 A | 4/1988 | Galloway | |
| 4,739,758 A | 4/1988 | Lai et al. | |
| 4,878,905 A | 11/1989 | Blass et al. | |
| 4,899,747 A | 2/1990 | Garren et al. | |
| 4,908,011 A | 3/1990 | Jacobsen et al. | |
| 4,925,446 A | 5/1990 | Garay et al. | |
| 5,052,998 A | 10/1991 | Zimmon | |
| 5,084,061 A | 1/1992 | Gau et al. | |
| 5,129,915 A | 7/1992 | Cantenys et al. | |
| 5,234,454 A | 8/1993 | Bangs | |
| 5,433,216 A | 7/1995 | Sugrue et al. | |
| 5,536,274 A | 7/1996 | Neuss | |
| 5,578,048 A | 11/1996 | Pasqualucci et al. | |
| 5,732,715 A | 3/1998 | Jacobs et al. | |
| 5,827,304 A | 10/1998 | Hart | |
| 5,976,106 A | 11/1999 | Verin et al. | |
| 5,985,307 A | 11/1999 | Hanson et al. | |
| 6,183,461 B1 | 2/2001 | Matsuura et al. | |
| 6,245,040 B1 | 6/2001 | Inderbitzen et al. | |
| 6,364,686 B2 | 4/2002 | Gimbel | |
| 6,364,868 B1 | 4/2002 | Ikeguchi | |
| 6,569,173 B1 | 5/2003 | Blatter et al. | |
| 6,616,678 B2 | 9/2003 | Nishtala et al. | |
| 6,656,194 B1 | 12/2003 | Gannoe et al. | |
| 6,712,831 B1* | 3/2004 | Kaplan et al. | 606/153 |
| 6,743,198 B1* | 6/2004 | Tihon | 604/104 |
| 6,746,460 B2 | 6/2004 | Gannoe et al. | |
| 7,004,176 B2 | 2/2006 | Lau | |
| 7,033,384 B2 | 4/2006 | Gannoe et al. | |
| 7,147,665 B1 | 12/2006 | Bryan et al. | |
| 7,347,868 B2 | 3/2008 | Burnett et al. | |
| 7,628,821 B2 | 12/2009 | Stack et al. | |
| 7,654,950 B2 | 2/2010 | Yachia et al. | |
| 7,883,524 B2 | 2/2011 | Chen | |
| 2001/0020150 A1 | 9/2001 | Ravo | |
| 2002/0045914 A1 | 4/2002 | Roberts et al. | |
| 2002/0055757 A1 | 5/2002 | Torre et al. | |
| 2002/0151923 A1 | 10/2002 | Holzer | |
| 2003/0158569 A1 | 8/2003 | Wazne | |
| 2003/0171768 A1 | 9/2003 | McGhan | |
| 2003/0191492 A1 | 10/2003 | Gellman et al. | |
| 2004/0030347 A1 | 2/2004 | Gannoe et al. | |
| 2004/0044357 A1 | 3/2004 | Gannoe et al. | |
| 2004/0059289 A1 | 3/2004 | Garza Alvarez | |
| 2004/0088008 A1 | 5/2004 | Gannoe et al. | |
| 2004/0093091 A1 | 5/2004 | Gannoe et al. | |
| 2004/0167625 A1 | 8/2004 | Beyar et al. | |
| 2004/0193092 A1 | 9/2004 | Deal | |
| 2004/0225247 A1 | 11/2004 | Pugsley et al. | |
| 2004/0267378 A1 | 12/2004 | Gazi et al. | |
| 2005/0004430 A1 | 1/2005 | Lee et al. | |
| 2005/0033331 A1 | 2/2005 | Burnett et al. | |
| 2005/0033345 A1 | 2/2005 | DeLegge | |
| 2005/0055039 A1* | 3/2005 | Burnett et al. | 606/151 |
| 2005/0070937 A1 | 3/2005 | Jambor et al. | |
| 2005/0085923 A1 | 4/2005 | Levine et al. | |
| 2005/0096750 A1 | 5/2005 | Kagan et al. | |
| 2005/0125020 A1 | 6/2005 | Meade et al. | |
| 2005/0192614 A1 | 9/2005 | Binmoeller | |
| 2005/0192629 A1 | 9/2005 | Saadat et al. | |
| 2005/0216040 A1 | 9/2005 | Gertner et al. | |
| 2005/0228504 A1 | 10/2005 | Demarais | |
| 2005/0267361 A1 | 12/2005 | Younker et al. | |
| 2005/0267595 A1 | 12/2005 | Chen et al. | |
| 2005/0267596 A1 | 12/2005 | Chen et al. | |
| 2006/0020278 A1* | 1/2006 | Burnett et al. | 606/153 |
| 2006/0058892 A1 | 3/2006 | Lesh et al. | |
| 2006/0100479 A1 | 5/2006 | Yachia et al. | |
| 2006/0142731 A1 | 6/2006 | Brooks | |
| 2006/0190019 A1 | 8/2006 | Gannoe et al. | |
| 2006/0206064 A1 | 9/2006 | Kagan et al. | |
| 2006/0271088 A1 | 11/2006 | Alfrhan | |
| 2007/0083224 A1 | 4/2007 | Hively | |
| 2007/0088380 A1 | 4/2007 | Hirszowicz et al. | |
| 2007/0149994 A1 | 6/2007 | Sosnowski et al. | |
| 2007/0173881 A1* | 7/2007 | Birk et al. | 606/192 |
| 2007/0239284 A1 | 10/2007 | Skerven et al. | |
| 2009/0164028 A1 | 6/2009 | Chen | |
| 2009/0171382 A1 | 7/2009 | Dillon et al. | |

FOREIGN PATENT DOCUMENTS

| | | |
|---|---|---|
| CA | 2483335 | 3/2005 |
| DE | 3227585 | 5/1983 |
| DE | 3227585 A1 | 5/1983 |
| DE | 3326061 | 2/1984 |
| DE | 3326061 A1 | 2/1984 |
| DE | 3310234 | 9/1984 |
| DE | 3310234 A1 | 9/1984 |
| DE | 3540936 | 10/1986 |
| DE | 3540936 C1 | 10/1986 |
| EP | 0246999 | 11/1987 |
| EP | 1342458 | 9/2003 |
| EP | 1342458 B1 | 8/2005 |
| GB | 2139902 | 11/1984 |
| IT | 1235492 | 9/1992 |
| IT | 1235492 B | 9/1992 |
| JP | 2008517677 | 5/2008 |
| WO | 8606611 | 11/1986 |
| WO | 8700034 | 1/1987 |
| WO | 9856321 | 12/1998 |
| WO | WO9856321 A1 | 12/1998 |
| WO | 0166166 | 9/2001 |
| WO | 0240081 | 5/2002 |
| WO | 03055420 | 7/2003 |
| WO | 03095015 | 11/2003 |
| WO | 2004014237 | 2/2004 |
| WO | 2004089262 | 10/2004 |
| WO | 2004105622 | 12/2004 |
| WO | 2005009288 | 2/2005 |
| WO | WO2004089262 A3 | 3/2005 |
| WO | 2005039457 | 5/2005 |
| WO | WO2005039457 A1 | 5/2005 |
| WO | 2005094257 | 10/2005 |
| WO | 2005107641 | 11/2005 |
| WO | 2006047708 | 5/2006 |
| WO | 2006070361 | 7/2006 |
| WO | WO2008132745 A2 | 11/2008 |
| WO | WO2007110866 A3 | 4/2009 |

OTHER PUBLICATIONS

U.S. Appl. No. 60/815,624.

Kadakia, SC et al., "Esophageal dilation with polyvinyl bougies using a marked guidewire without the aid of fluoroscopy," Am J Gastro 88:1381-86, 1993.

Fleischer, D.E. et al., "A marked guidewire facilitates esophageal dilation," Am J Gastro 84:359-61, 1989.

Dumon, J.R. et al., "A new method of esophageal dilation using Savary-Gilliard Bougies," Gastro Endosc 31:379-82, 1985.

Werth, et al., "A safe and quick method for endoscopic retrieval of multiple gastric foreign bodies using a protective sheath," Surg Gynecol Obstet 171(5):419-20, 1990.

U.S. Appl. No. 60/639,843.

An International Search Report dated Feb. 10, 2011, which issued during the prosecution of Applicant's PCT/IL10/00833.

An Office Action dated Dec. 30, 2009, which issued during the prosecution of Applicant's U.S. Appl. No. 11/132,855.

An Office Action dated Apr. 26, 2011, which issued during the prosecution of Japanese Patent Application No. JP 548959/2007 (an English translation is attached).

An office action issued in a corresponding Japanese application 2009-502330 dated Feb. 17, 2012.

An office action issued in U.S. Appl. No. 11/132,855 dated Mar. 27, 2012.

An office action issued in U.S. Appl. No. 11/721,993 dated Feb. 27, 2012.

European Search Report dated Aug. 22, 2011 which issued during the prosecution of Applicant's EP Application No. 11161677.7.

An Office Action dated Dec. 13, 2011, which issued during the prosecution of U.S. Appl. No. 12/598,110.

An Office Action dated Oct. 16, 2008, which issued during the prosecution of Applicant's U.S. Appl. No. 11/132,855.

An Office Action dated Jun. 11, 2009, which issued during the prosecution of Applicant's U.S. Appl. No. 11/132,855.

An Office Action dated Aug. 24, 2011, which issued during the prosecution of Applicant's U.S. Appl. No. 11/132,855.

An English Translation of an Office Action dated Apr. 13, 2010, which issued during the prosecution of Applicant's Chinese Patent Application No. 200580048692.6.

An International Search Report dated May 28, 2008, which issued during the prosecution of Applicant's PCT/IL05/01381.

An International Search Report dated Dec. 23, 2008, which issued during the prosecution of Applicant's PCT/IL08/00579.

An International Search Report dated Sep. 22, 2008, which issued during the prosecution of Applicant's PCT/IL07/00398.

Andersen et al, "Randomised trial of endoscopic endoprosthesis versus operative bypass in malignant obstructive jaundice", Gut, 30, 1132-1135 (1989).

Parker et al. "Esophageal dilation with polyvinyl bougies, using a marked guidewire without the aid of fluoroscopy: an update", Am J Gastroenterol. (Sep. 1993); 88(9):1381-6—an abstract.

Borowski A et al., "Minimally Invasive, Nonendoscopic Saphenectomy for Coronary Bypass Surgery", J Card Surg 16 (6): 484-6, (2001)—an abstract.

Cope, "Improved Anchoring of Nephrostomy Catheters: Loop Technique", American J of Roetngenology 1980.

Dondelinger et al, "Percutaneous management of intraperitoneal, hepatic and other fluid collections", Baillieres Clin Gastroenterol (1992).

Dumon et al, "A new method of esophageal dilation using Savary-Gilliard bougies", Gastro Endosc. (1985).

Gronval et al , "Ultrasound-guided Drainage of Fluid-containing Masses Using Angiographic Catheterization Techniques", Am J Roetgenol (1977).

Lambiase, "Percutaneous Abscess and Fluid Drainage: A Critical Review", Cardiovascular and interventional radiology 14: 143-157 (1991).

Speer et al, "Randomised Trial of Endoscopic Versus Percutaneous Stent Insertion in Malignant Obstructive Jaundice", The Lancet (1987).

Shepherd et al, "Endoscopic biliary endoprosthesis in the palliation of malignant obstruction of the distal common bile duct: a randomized trial", British journal of surgery, vol. 75, pp. 1166-1168 (1988).

Van sonnenberg et al, "Percutaneous Abscess Drainage: Current Concepts", Radiology (1991).

Office Action issued in U.S. Appl. No. 12/903,448 dated Sep. 18, 2012.

Japanese Examination Report Mailed Oct. 16, 2012 in Japanese Application No. 2011-056619.

* cited by examiner

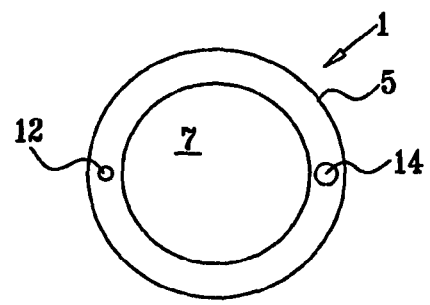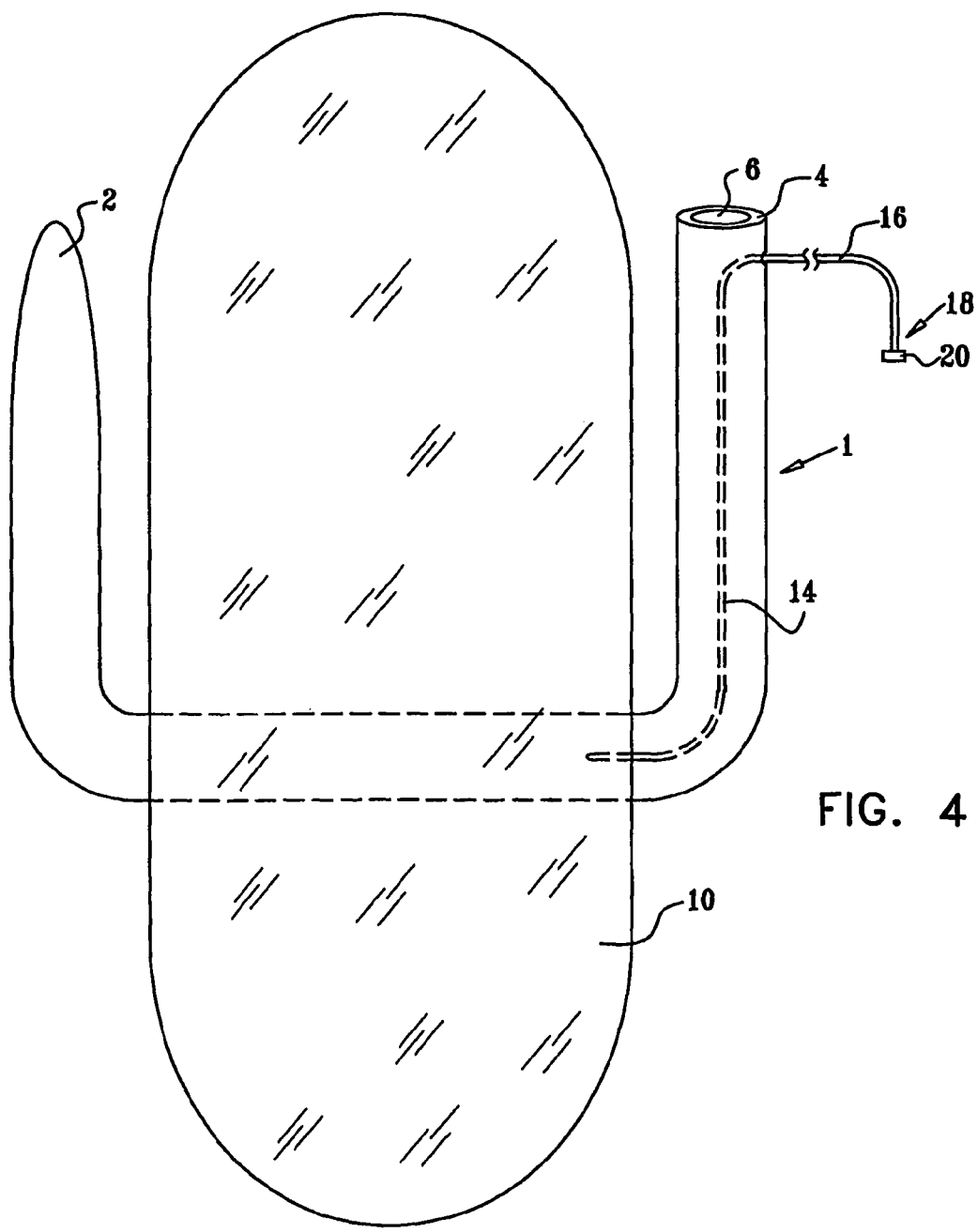

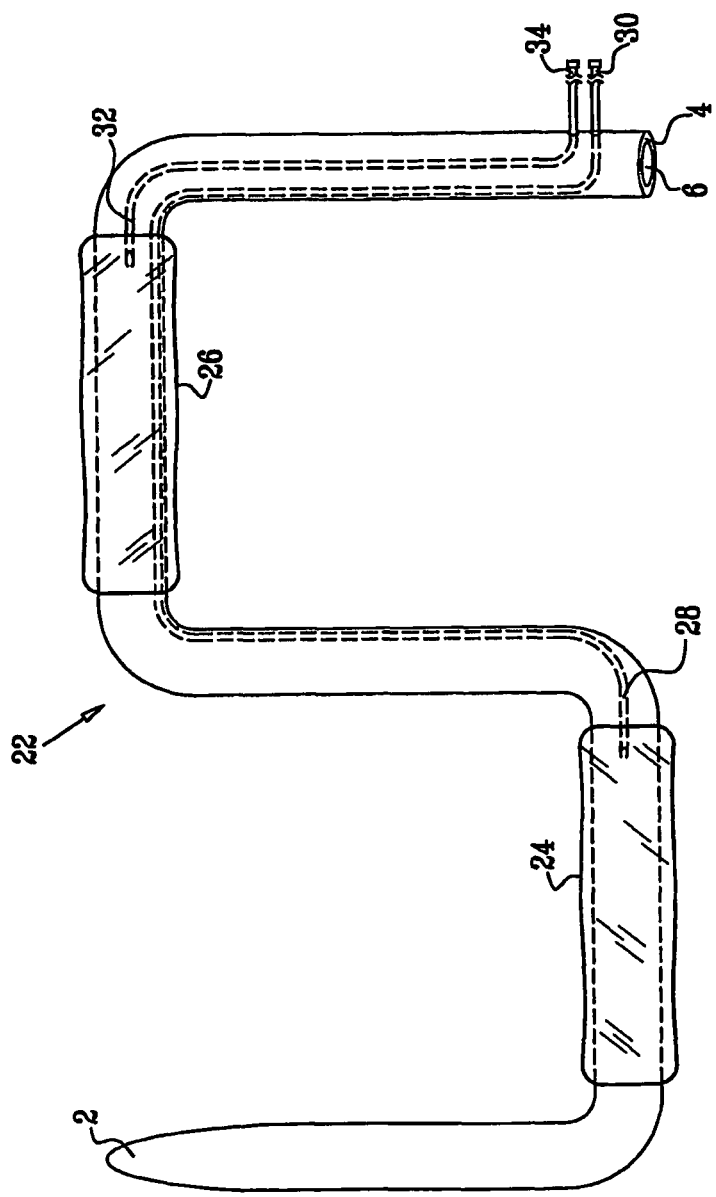

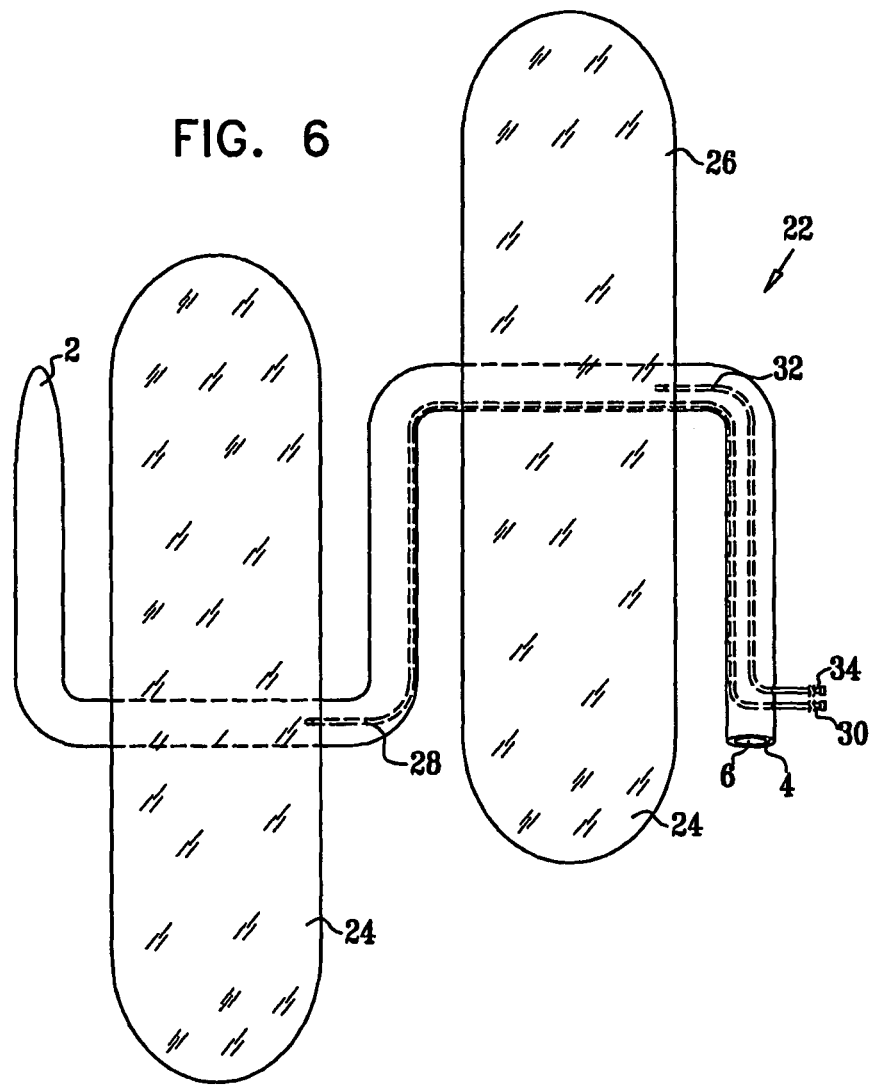

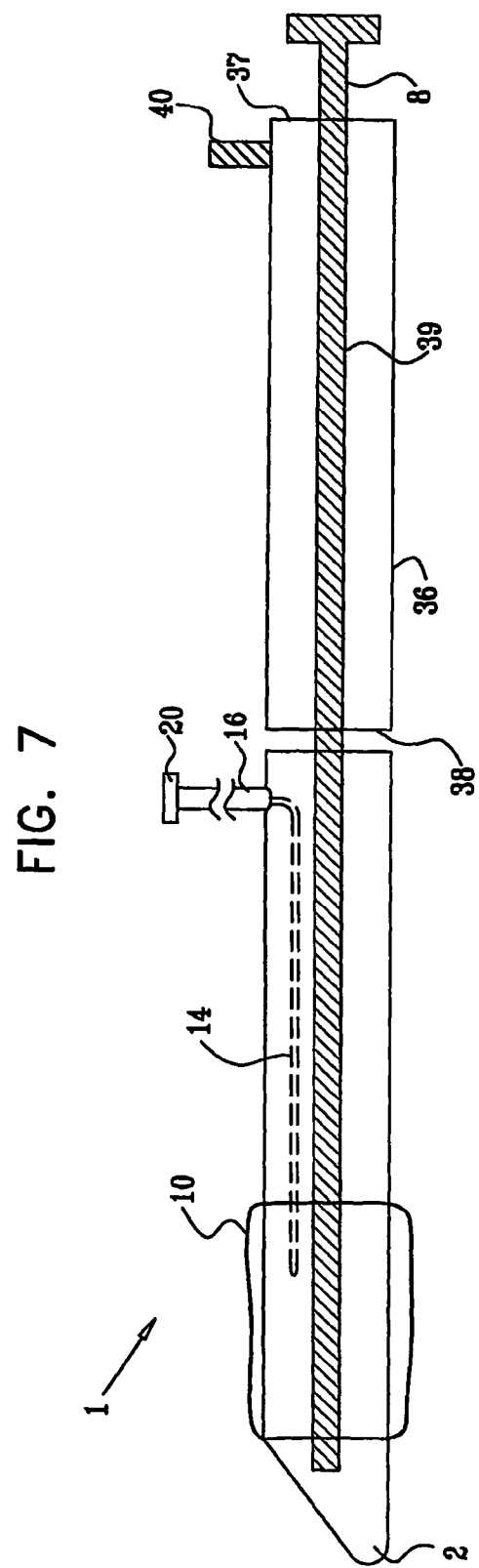

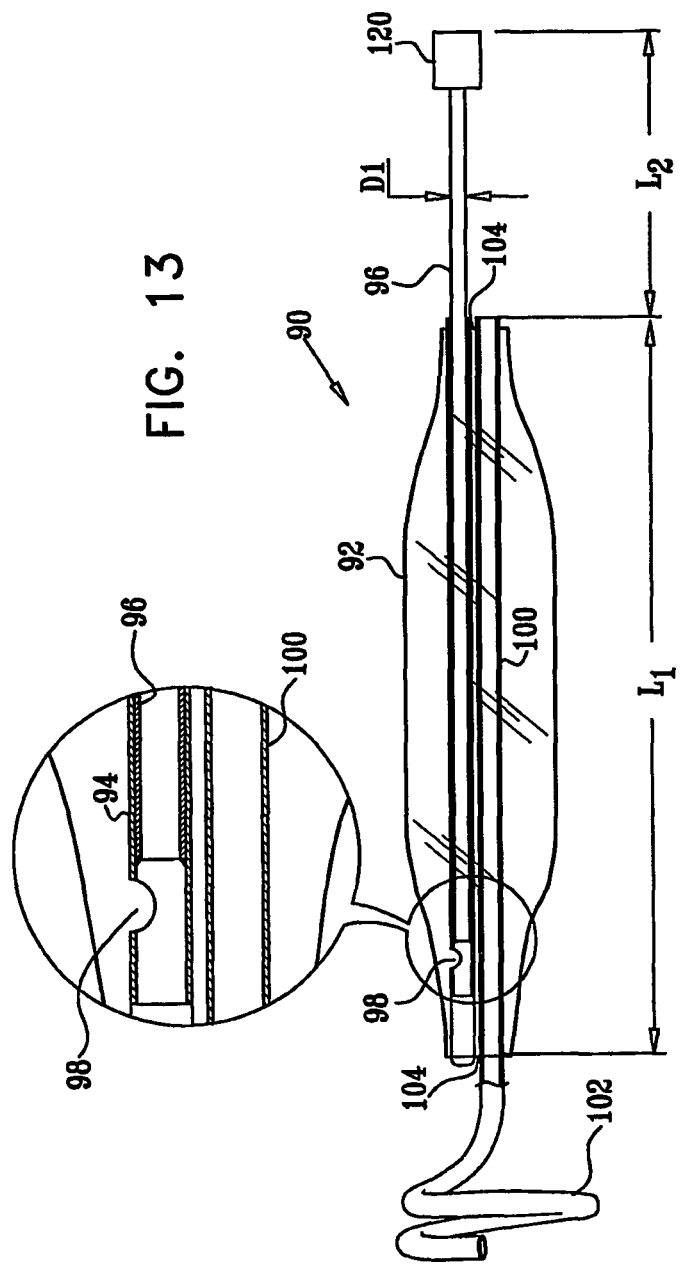

FIG. 17A
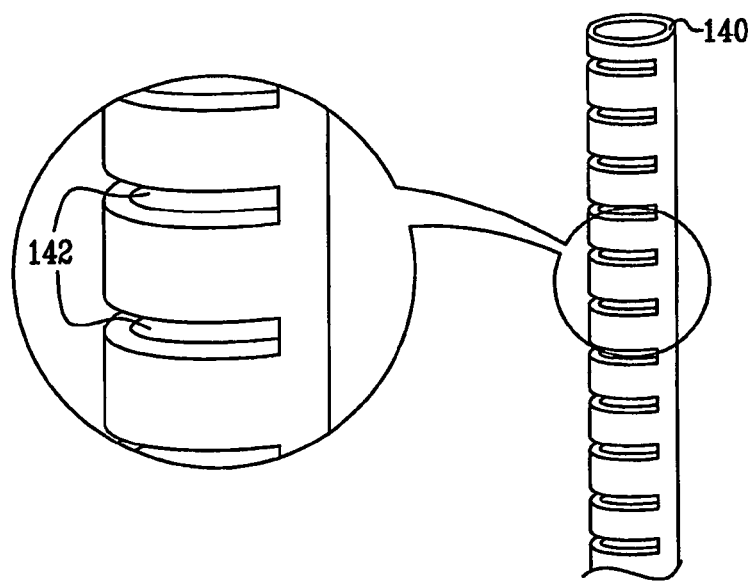
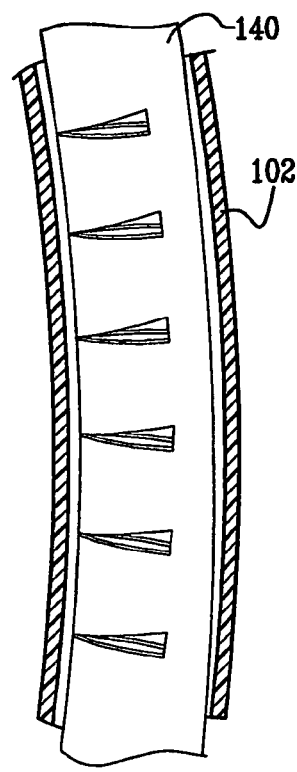
FIG. 17B

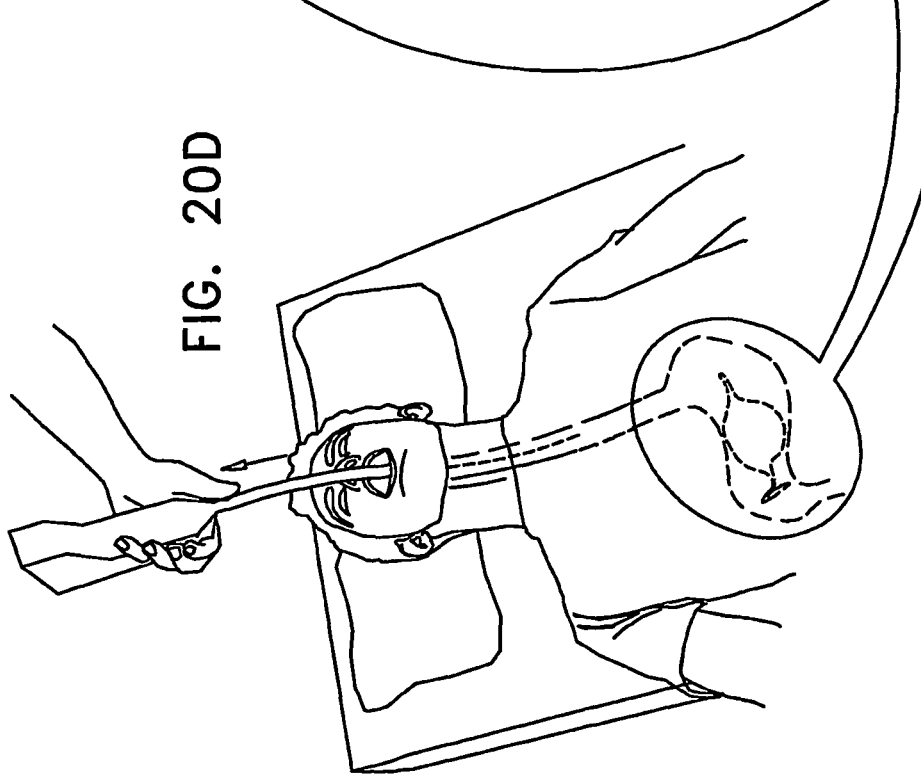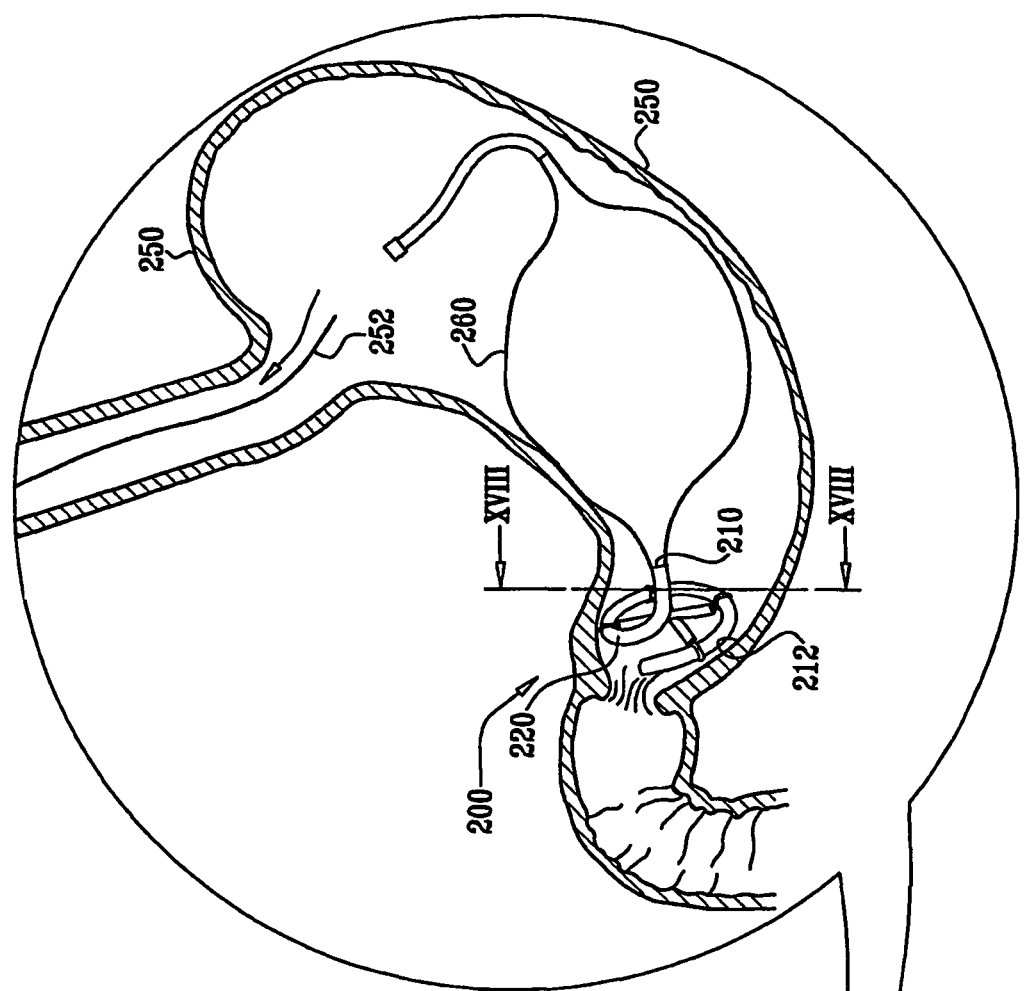
FIG. 20D

FLOATING GASTROINTESTINAL ANCHOR

CROSS-REFERENCES TO RELATED APPLICATIONS

The present application is the US national phase application of PCT/IL2007/000398 to Brooks, filed Mar. 28, 2007, which claims priority from:

U.S. Provisional Patent Application 60/787,124 to Brooks, filed Mar. 28, 2006, entitled, "Floating gastrointestinal anchor"; and U.S. Provisional Patent Application 60/815,624 to Brooks, filed Jun. 21, 2006, entitled, "Floating gastrointestinal anchor."

Each of the above applications is assigned to the assignee of the present invention and is incorporated herein by reference.

FIELD OF THE INVENTION

The present invention generally relates to inplantable medical apparatus. Specifically, the present invention relates to apparatus for implantation in the gastrointestinal tract.

BACKGROUND OF THE INVENTION

Morbid obesity remains an ever-growing problem in the U.S. Varying forms of gastric bypass surgery have developed and have improved over the last few decades. Recently, laparoscopic gastric banding has emerged as a less invasive surgical option. However, bariatric surgery is fraught with morbidity of up to 20%, with a re-operation rate approaching 25% at 3-5 years post-op. Bariatric surgery carries an operative mortality of 0.5%. Diet and pharmaceutical alternatives have not been very effective, with a high recidivism rate. Today, the Bioenterics® intragastric balloon (BIB®) (Inamed Corporation, Santa Barbara, Calif., USA) is in use outside of the U.S., achieving average weight loss of 15 kg and 5 point drop in BMI. However, an 8-9% balloon deflation rate has resulted in unwarranted migration leading to obstruction.

PCT Patent Publication WO 06/070361 to Brooks, which is incorporated herein by reference, describes apparatus for use in a gastrointestinal tract of a subject. The apparatus includes a straightening rod, and a flexible tubular anchor having a distal end and an open proximal end, and sized to fit in the gastrointestinal tract. The anchor comprises a material that has an elastic memory which biases the anchor towards assuming a pre-selected bent configuration. The anchor is shaped so as to define a central core extending from the open proximal end toward the distal end. The anchor is configured to be straightened from the pre-selected bent configuration by insertion of the straightening rod in the central core. The apparatus further includes a device coupled to the anchor, selected from the list consisting of: a therapeutic device, and a transmitting device.

US Patent Application Publication 2004/0044357 to Gannoe et al., which is incorporated herein by reference, describes gastric space occupying devices that include a stent configured for deployment in the gastrointestinal tract of a patient, and in particular, for deployment in the esophagus or the stomach. Secured to the stent is an expandable member that is adapted to reside within the patients stomach. When expanded, the expandable member occupies a predefined volume within the patient's stomach and is further tethered to the deployed stent, thereby retaining or anchoring the expandable member within the stomach. Methods and systems for the deploying the space occupying devices are also described.

PCT Publication WO 05/107641, US Patent Application Publication 2005/0267596, and US Patent Application Publication 2005/0267595 to Chen et al., which are incorporated herein by reference, describe a gastric balloon that includes a scaffold structure, one or more internal inflatable compartments within the scaffold structure, and one or more inflatable bladders formed over the space-filling compartment. The gastric balloon may be deployed transesophageally using a gastroscope, and is inflated in situ, preferably using a combination of liquid and gas inflation media.

PCT Publication WO 05/009288 and US Patent Application Publication 2005/0033331 to Burnett et al., which are incorporated herein by reference, describe techniques for facilitating intermittent and/or partial obstruction of a pyloric valve. Devices described generally include a support portion for preventing the device from passing through the pyloric valve, and a tissue engagement portion for contacting tissue adjacent the pyloric valve to obstruct the valve. Some embodiments also include a positioning member extending from the tissue engagement portion for helping position the device for obstructing the valve. A retaining member may optionally be included on the distal end of the positioning member for further maintaining a position of the device in the stomach. Some embodiments are deliverable into the stomach through the esophagus, either by swallowing or through a delivery tube or catheter. Some embodiments are described as being fully reversible. Some embodiments self-expand within the stomach, while others are inflated or otherwise expanded.

US Patent Application Publication 2005/0055039 to Burnett et al., which is incorporated herein by reference, describes a device for performing one or more functions in a gastrointestinal tract of a patient, which includes an anchoring member and at least one actuator, sensor, or combination of both coupled with the anchoring device. The anchoring device is adapted to maintain at least part of the device within a pyloric portion of the patient's stomach and to intermittently engage, without directly attaching to, stomach tissue. Actuators perform ally suitable function, such as transmitting energy to tissue, acting as a sleeve to reduce nutrient absorption, occupying space in the stomach, eluting a drug and/or the like. Sensors may be adapted to sense any suitable patient characteristic within the patient's gastrointestinal tract, such as pH, temperature, bile content, nutrient content, fats, sugars, alcohol, opiates, drugs, analytes, electrolytes and/or hemoglobin.

US Patent Application Publication 2006/0020278 to Burnett et al., which is incorporated herein by reference, describes methods, devices and systems which facilitate gastric retention of a variety of therapeutic devices. Devices generally include a support portion for preventing the device from passing through the pyloric valve or esophagus. A retaining member may optionally be included on the distal end of the positioning member and is described to maintain a position of the device in the stomach. Some embodiments are deliverable into the stomach through the esophagus, either by swallowing or through a delivery tube or catheter. Some embodiments are fully reversible. Some embodiments self-expand within the stomach, while others are inflated or otherwise expanded.

PCT Publication WO 05/094257 to Birk, which is incorporated herein by reference, describes a gastric balloon and method of adding and removing fluid therefrom. The gastric balloon includes a shell, a receiver, and a retractable tubing housed in the receiver and extendable from the stomach of a patient to the mouth of the patient. The shell is inflated and deflated from outside the body of the patient. The method of adding or removing fluid from the implanted gastric balloon includes steps of inserting a gastroscopic tool into the stomach of a patient and grasping an end of a retractable tubing housed in a receiver of the gastric balloon. Further steps of the method include withdrawing at least a portion of the retractable tubing from the stomach and out of a patient's mouth and adding or removing fluid from the gastric balloon via the retractable tubing withdrawn from the patient.

The following patents and patent application publications, which are incorporated herein by reference, may be of interest.

U.S. Pat. No. 7,033,384 to Gannoe, et al.
US Patent Application Publication 2006/0190019 to Gannoe et al.
US Patent Application Publication 2002/0055757 to Tone et al.
US Patent Application Publication 2005/0228504 to Demarais
US Patent Application Publication 2005/0085923 to Levine et al.
US Patent Application Publication 2005/0192614 to Binmoeller
US Patent Application Publication 2004/0267378 to Gazi et al.
U.S. Pat. No. 4,416,267 to Garren et al.
U.S. Pat. No. 4,925,446 to Garay et al.
U.S. Pat. No. 5,052,998 to Zimmon
PCT Publication WO 05/039457 to Paganon et al.
PCT Publication WO 04/089262 to Paganon
Canadian Patent Application Publication 2483335 to Byrum et al.
US Patent Application Publication 2005/0070937 to Jambor et al.
US Patent Application Publication 20005/004430 to Lee et al.
PCT Publication WO 04/105622 to Ritchie
US Patent Application Publication 2004/088008 to Gannoe et al.
PCT Publication WO 04/014237 to Gannoe et al.
US Patent Application Publication 2004/093091 to Gannoe et al.
US Patent Application Publication 2004/059289 to Garza et al.
PCT Publication WO 03/095015 to Alverdy
European Patent Application Publication EP 1342458 to Creusy et al.
US Patent Application Publication 2003/158569 to Wazne
PCT Publication WO 03/055420 to Lointier et al.
U.S. Pat. No. 6,656,194 to Gannoe et al.
US Patent Application Publication 2003/171768 to McGhan
PCT Publication WO 02/40081 to Bales et al.
PCT Publication WO 01/66166 to Birk
PCT Publication WO 98/56321 to Pier et al.
U.S. Pat. No. 5,234,454 to Bangs
Canadian Patent Application Publication CA 2068715 to Kuzmak
U.S. Pat. No. 4,696,288 to Kuzmak et al.
U.S. Pat. No. 5,129,915 to Cantenys
U.S. Pat. No. 5,084,061 to Gau et al.
U.S. Pat. No. 4,908,011 to Jacobsen et al.
European Patent Application Publication EP 0246999 to Eshel et al.
PCT Publication WO 87/00034 to Taylor
U.S. Pat. No. 4,739,758 to Lai et al.
PCT Publication WO 86/06611 to Kullas et al.
U.S. Pat. No. 4,694,827 to Weiner et al.
German Patent Application Publication DE 3540936 to Stricker et al.
British Patent Application Publication GB 2139902 to Celestin et al.
Canadian Patent Application Publication CA 1233387 to Garren et al.
U.S. Pat. No. 4,899,747 to Garren et al.
German Patent Application Publication DE 3326061 to Woerner
German Patent Application Publication DE 3310234 to Husfeldt
Italian Patent IT 1235492 to Frimberger et al.
U.S. Pat. No. 4,485,805 to Foster
German Patent Application Publication DE 3227585 to Woerner
U.S. Pat. No. 4,416,267 to Garren et al.
U.S. Pat. No. 4,315,509 to Smit
U.S. Pat. No. 7,004,176 to Lau The following articles, which are incorporated herein by reference, may be of interest:

Kadakia S C et al., "Esophageal dilation with polyvinyl bougies using a marked guidewire without the aid of fluoroscopy," Am J Gastro 88:1381-86 (1993)

Fleischer D E et al., "A marked guidewire facilitates esophageal dilation," Am J Gastro 84:359-61 (1989)

Dumon J R et al., "A new method of esophageal dilation using Savary-Gilliard bougies," Gastro Endosc 31:379-82 (1985)

Werth et at., "A safe and quick method for endoscopic retrieval of multiple gastric foreign bodies using a protective sheath," Surg Gynecol Obstet 171(5):419-20 (1990)

SUMMARY OF THE INVENTION

According to one aspect of the invention, a flexible tubular anchor having an elastic memory for assuming a pre-selected bent configuration is described for placement in the gastrointestinal tract. The anchor comprises a distal end and an open proximal end having a central core extending toward the distal end. When the core receives a straightening rod therethrough, the anchor is straightened from its pre-selected bent shape.

In accordance with another aspect of the invention, a method of inserting a flexible tubular anchor in a subject's gastrointestinal tract is described. The anchor has an elastic memory for assuming a pre-selected bent shape and has a distal end, an open proximal end having a central core extending toward the distal end, a balloon sealed along a portion of the anchor, an inflation conduit extending from the proximal end to the interior of the balloon, a pushing catheter having a bore therethrough axially aligned with the anchor, and a straightening rod extending through said catheter and the anchor. The method generally comprises inserting the anchor in its straightened configuration into the subject's stomach, separating the anchor from the straightening rod thereby allowing the anchor to assume its pre-selected bent shape, and then inflating the balloon.

In some embodiments of the present invention, a floating gastrointestinal anchor comprises a flexible tube, which, in its relaxed position, is shaped so as to define a generally planar base portion, and a proximal portion that projects away from the plane defined by the base portion, typically in an approximately perpendicular direction. The anchor further comprises at least two cross-bar elements, the ends of which are positioned in a vicinity of the base portion of the anchor. The cross-bar elements help maintain the shape of the anchor. The anchor typically, but not necessarily, is positioned in an antrum, adjacent to the pyloric valve, and to some extent interferes with natural antral contractions, thereby slowing gastric emptying and enhancing the sensation of satiety. The proximal portion of the anchor is typically, but not necessarily, coupled to a device, such as a therapeutic device, e.g., a balloon.

Typically, each of the cross-bar elements is shaped so as to define a lumen therethrough, and comprises an elastic coupling band that passes through the lumen. Two portions of each of the coupling bands protrude from the cross-bar element, and are coupled to the base portion of the anchor at two respective points that are approximately opposite one another. In order to enable transesophageal insertion of the anchor using a gastroscope, the anchor is typically stretched until it assumes an elongated position, in which the tube thereof is generally straight. The elastic coupling bands of the cross-bar elements enable the anchor to assume this elongated position, in which the cross-bar elements are displaced from their relaxed positions until they are approximately parallel with the tube of the anchor. A generally stiff rod is inserted into a lumen of the tube, in order to maintain the stretched position during insertion. Once the anchor has been appropriately positioned in the stomach, the rod is removed, allowing the anchor to assume its relaxed position.

As will be appreciated by those persons skilled in the art, a feature provided by some embodiments of the present invention is the ease in which an anchor may be inserted into the gastrointestinal system. Another feature provided by some embodiments of the present invention is the safety and security provided by the use of such an anchor. It is therefore an object of some embodiments of the present invention to provide a safe and easy method of inserting and securing a floating anchor into the gastrointestinal system so that a variety of devices may be safely secured therein. It is another object of some embodiments of the present invention to safely and securely anchor a balloon in the stomach for promoting a feeling of satiety in a subject. Additional objects of embodiments of the present invention will become apparent from the following description.

There is therefore provided, in accordance with an embodiment of the present invention, apparatus for use in a gastrointestinal tract of a subject, the apparatus including:

a straightening rod;

a flexible tubular anchor having a distal end and an open proximal end, and sized to fit in the gastrointestinal tract, the anchor including a material that has an elastic memory which biases the anchor towards assuming a pre-selected bent configuration, the anchor shaped so as to define a central core extending from the open proximal end toward the distal end, and the anchor configured to be straightened from the pre-selected bent configuration by insertion of the straightening rod in the central core; and a device coupled to the anchor, selected from the list consisting of: a therapeutic device, and a transmitting device.

For some applications, the distal end of the anchor is tapered. For some applications, the bent configuration is selected from the group consisting of: a C-shaped configuration, an S-shaped configuration, a U-shaped configuration, a helical configuration, and a sinusoidal configuration, and the material has the elastic memory which biases the anchor towards assuming the selected bent configuration.

For some applications, the apparatus includes a pushing catheter shaped so as to define a bore therethrough, the catheter adapted to be axially aligned with the anchor, and the straightening rod is configured to be inserted through the catheter into the central core of the anchor.

In an embodiment, the anchor is shaped so as to define a wall having a guide wire canal therein.

In an embodiment, the device includes a transmitting device.

In an embodiment, the anchor is adapted to interfere with gastric emptying of the subject.

In an embodiment, the device includes the therapeutic device. For some applications, the therapeutic device includes string-like attachments. For some applications, the therapeutic device includes a medication administration device. For some applications, the therapeutic device is adapted to administer tumor-targeting therapy.

In an embodiment, the therapeutic device includes an attachment adapted to interfere with gastric emptying of a stomach of the subject when the anchor is placed in the stomach.

In an embodiment, the therapeutic device includes a balloon coupled to a balloon-coupling portion of the anchor. For some applications, the anchor includes a conduit wrapped around an external surface of the anchor, the conduit extending from the proximal end of the anchor to an interior of the balloon.

In an embodiment, the balloon is adapted to promote a feeling of satiety in the subject. Alternatively or additionally, the balloon is adapted to interfere with peristaltic waves and gastric emptying of the subject.

For some applications, the balloon includes a first balloon, and the therapeutic device includes a second balloon.

In an embodiment, the balloon is positioned around the balloon-coupling portion of the anchor. For some applications, the anchor includes proximal and distal portions on respective sides of the balloon-coupling portion, and the balloon is coupled to the balloon-coupling portion and is not coupled to the proximal or distal portions. For some applications, a length of the balloon-coupling portion of the anchor is less than 75% of a total length of the anchor, such as less than 50% of the total length of the anchor.

In an embodiment, the anchor is shaped so as to define a conduit channel extending from the proximal end of the anchor to an interior of the balloon. For some applications, the apparatus includes a conduit having distal and proximal ends, which is adapted to be placed through the conduit channel, such that the distal end opens to the interior of the balloon, and the proximal end opens outside of the anchor.

In an embodiment, a distal portion of the anchor has a curved shape when the anchor assumes the bent configuration. For some applications, the distal portion of the anchor has a helical shape when the anchor assumes the bent configuration. For some applications, a proximal portion of the anchor has a helical shape when the anchor assumes the bent configuration.

In an embodiment, a proximal portion of the anchor has a curved shape when the anchor assumes the bent configuration. For some applications, the proximal portion of the anchor has a helical shape when the anchor assumes the bent configuration.

In an embodiment, the anchor includes all elongated appendage extending from the distal end thereof, the appendage having a distal end, the appendage configured to assume a position in which the distal end thereof is in a vicinity of the proximal end of the anchor when the anchor assumes the bent configuration. For some applications, the appendage includes a housing and a wire therein, and the wire includes a first flexible segment, a second relatively stiff segment, and a third relatively flexible segment. For some applications, the device includes a balloon coupled to the anchor, and the appendage is adapted to be displaced by the balloon when the balloon is inflated, such that the distal end of the appendage is not in the vicinity of the proximal end of the anchor.

There is further provided, in accordance with an embodiment of the present invention, apparatus for use in a gastrointestinal tract of a subject, the apparatus including:
a straightening rod;
a flexible tubular anchor having a closed distal end and an open proximal end, the anchor including a material that has an elastic memory which biases the anchor towards assuming a pre-selected bent configuration, the anchor shaped so as to define a central core extending from the open proximal end toward the distal end, and the anchor configured to be straightened from the pre-selected bent configuration by insertion of the straightening rod in the central core.

There is yet further provided, in accordance with an embodiment of the present invention, apparatus for use in a stomach of a subject, the apparatus including:
an elongated biocompatible anchor having proximal and distal portions and a balloon-coupling portion therebetween, the anchor being sized to fit in the stomach; and
a balloon coupled to the balloon-coupling portion of the anchor, and not to the proximal or distal portions.

In an embodiment, the balloon is adapted to promote a feeling of satiety in the subject. Alternatively or additionally, the balloon is adapted to interfere with peristaltic waves and gastric emptying of the subject.

In an embodiment, the anchor is adapted to interfere with gastric emptying of the subject.

In an embodiment, the anchor is adapted to assume a pre-selected bent configuration when in the stomach.

In an embodiment, the balloon is positioned around the balloon-coupling portion of the anchor. For some applications, a length of the balloon-coupling portion of the anchor is less than 75% of a total length of the anchor, such as less than 50% of the total length of the anchor.

There is still further provided, in accordance with an embodiment of the present invention, a method including:
straightening a flexible tubular anchor that includes a material that has an elastic memory which biases the anchor towards assuming a pre-selected bent configuration, by inserting a straightening rod into a central core extending from an open proximal end toward a distal end of the anchor;
inserting the straightened anchor with the rod therein into a gastrointestinal tract of a subject; and
removing the anchor from the rod, thereby allowing the anchor to assume the pre-selected bent configuration.

For some applications, inserting the straightened anchor includes threading the anchor onto a guidewire. Alternatively, inserting the straightened anchor includes inserting the anchor into an overtube.

For some applications, inserting the rod into the central core includes inserting the rod through a bore of a pushing catheter axially aligned with the anchor, and then into the central core, and removing the rod from the anchor includes pushing the anchor off the rod by pushing on the pushing catheter.

For some applications, inflating the balloon includes inserting an inflation conduit into the gastrointestinal tract, and inflating the balloon via the inflation conduit. For some applications, inflating the balloon includes inflating the balloon via an inflation conduit that passes through the conduit channel.

There is additionally provided, in accordance with an embodiment of the present invention, method including:
inserting, into a stomach of a subject, art elongated anchor having proximal and distal portions and a balloon-coupling portion therebetween;
inflating a balloon coupled to the balloon-coupling portion of the anchor, and not to the proximal or distal portions.

There is also provided, in accordance with an embodiment of the invention, apparatus for use in a stomach of a subject, the apparatus including:
a balloon, adapted for placement in the stomach;
an anchor, coupled to the balloon and adapted to prevent the balloon from passing into a duodenum of the subject; and
an inflation tube, coupled to the balloon to permit inflation of the balloon, and adapted to stretch from the stomach to a mouth of the subject to facilitate inflation of the balloon.

In an embodiment, the inflation tube is adapted to stretch to more than 2.5 times a resting length thereof, e.g., from 2.5 to 10 times the resting length (such as six times the resting length).

In an embodiment, the anchor includes a resilient tube, and the apparatus includes a bend-limiting tube coupled to the resilient tube, which limits an extent of bending of the resilient tube.

In an embodiment, the inflation tube is configured to be disposed within the resilient tube, the resilient tube permitting the inflation tube to assume a straight position, or to bend up to a predefined limit.

In an embodiment, the anchor includes a material that has an elastic memory which biases the anchor towards assuming a pre-selected bent configuration.

In an embodiment, the apparatus includes a straightening rod, and:
the anchor has a distal end and an open proximal end;
the anchor is shaped so as to define a central core extending from the open proximal end toward the distal end; and
the anchor is configured to be straightened from the pre-selected bent configuration by insertion of the straightening rod in the central core.

In an embodiment, the balloon is adapted to promote a feeling of satiety in the subject.

In an embodiment, the balloon is adapted to interfere with peristaltic waves and gastric emptying of the subject.

In an embodiment, the apparatus includes a device coupled to the anchor, selected from the list consisting of: a therapeutic device, and a transmitting device.

In an embodiment, the apparatus includes a closure mechanism coupled to a proximal end of the inflation tube, configured to maintain pressure within the balloon by preventing leakage of fluid therefrom into the stomach of the subject.

In an embodiment, the apparatus includes an extraction tool configured to stretch the inflation tube by reversibly engaging and pulling on the inflation tube.

In an embodiments the apparatus includes a filling tube configured to be temporarily coupled to the inflation tube while the inflation tube is stretched, and configured to facilitate inflation of the balloon when the inflation tube is relaxed at least in part following being stretched.

There is additionally provided, in accordance with an embodiment of the invention, a method, including:
inserting into a stomach of a subject a gastric balloon in fluid communication with an inflation tube;
assessing an inflation level of the balloon following insertion thereof;
in response to identifying a need for inflation of the balloon, stretching the inflation tube while keeping the balloon within the stomach; and
inflating the balloon following the stretching of the inflation tube.

In an embodiment, assessing the inflation level of the balloon includes determining a level of weight loss of the subject and correlating weight loss to the level of inflation of the balloon.

In an embodiment, inflating the balloon includes injecting a fluid into the inflation tube while a proximal end of the inflation tube is outside of a body of the subject.

In an embodiment, the method includes temporarily coupling the inflation tube to a filling tube following the stretching of the inflation tube, and wherein inflating the balloon includes:

allowing at least a portion of the inflation tube to return to the stomach while the filling tube is coupled to the inflation tube; and injecting a fluid into the inflation tube via the filling tube while the portion of the inflation tube remains disposed within the stomach.

In an embodiment, stretching the inflation tube includes extracting a proximal portion of the inflation tube from a mouth of the subject.

In an embodiment, extracting the proximal portion of the inflation tube includes stretching the inflation tube to at least 2.5 times a resting length thereof.

There is further provided, in accordance with an embodiment of the present invention, apparatus for use in a stomach of a subject, the apparatus including an anchor, which includes:

a flexible tube, which, when in a relaxed position, is shaped so as to define a generally planar base portion that prevents the anchor from passing into a duodenum of the subject; and at least two cross-bar elements having ends which are positioned in a vicinity of the base portion, which cross-bar elements are configured to help maintain a shape of the base portion.

In an embodiment, the anchor is configured to be positioned in an antrum of the stomach such that the anchor to some extent interferes with natural antral contractions of the antrum.

For some applications, the tube is shaped so as to define a proximal portion that projects away from a plane defined by the base portion, and the apparatus includes a balloon coupled to the proximal portion of the tube. For some applications, the anchor includes at least one sleeve that encloses one of the cross-bar elements.

In an embodiment, the cross-bar elements are shaped so as to define respective lumens therethrough, and the cross-bar elements include respective elastic coupling bands that pass through the respective lumens. For some applications, two portions of each of the coupling bands protrude from the respective cross-bar element, and are coupled to the base portion at two respective points that are approximately opposite one another on the base portion. For some applications, the anchor is configured, when stretched, to assume an elongated position in which the tube is generally straight, and in which the cross-bar elements are positioned approximately parallel with the tube.

The method and apparatus of the present invention will be better understood by reference to the following detailed discussion of specific embodiments and the attached figures, which illustrate and exemplify such embodiments.

BRIEF DESCRIPTION OF THE DRAWINGS

FIGS. 2 and 3 are a side view and a cross-sectional view, respectively, of another configuration of the anchor of FIG. 1, in accordance with an embodiment of the present invention;

FIG. 4 is a side view of the embodiment depicted in FIG. 2, showing an inflated balloon, in accordance with an embodiment of the present invention;

FIG. 5 is a side view of another floating gastrointestinal anchor, in accordance with an embodiment of the present invention;

FIG. 6 is a side view of the anchor of FIG. 5, showing balloons in an inflated state, in accordance with an embodiment of the present invention;

FIG. 7 is a side view of an embodiment of the anchor of FIG. 1 in a straightened position prior to insertion into the gastrointestinal tract, in accordance with an embodiment of the present invention;

FIGS. 13-16 are schematic illustrations of obesity treatment apparatus during different phases thereof, in accordance with an embodiment of the present invention;

FIGS. 17A and 17B are schematic illustrations of a bend-limiting tube for insertion into a gastrointestinal anchor, in accordance with an embodiment of the present invention;

FIGS. 20A-D are schematic illustrations of the deployment of the anchor of FIG. 18, in accordance with an embodiment of the present invention.

DETAILED DESCRIPTION OF EMBODIMENTS

The following preferred embodiments as exemplified by the drawings are illustrative of embodiments of the invention, and are not intended to limit the invention as encompassed by the claims of this invention.

A floating gastrointestinal anchor 1, as generally illustrated in the figures, is provided for securing devices in the gastrointestinal tract. The gastrointestinal tract, as used herein, includes the esophagus. Although devices and methods are described in some embodiments as being useful for anchoring an inflated balloon in the stomach for affecting weight loss, it is to be understood that the methods and devices described herein can be used for securing any device for its intended purpose anywhere in the gastrointestinal tract.

Figure 1:
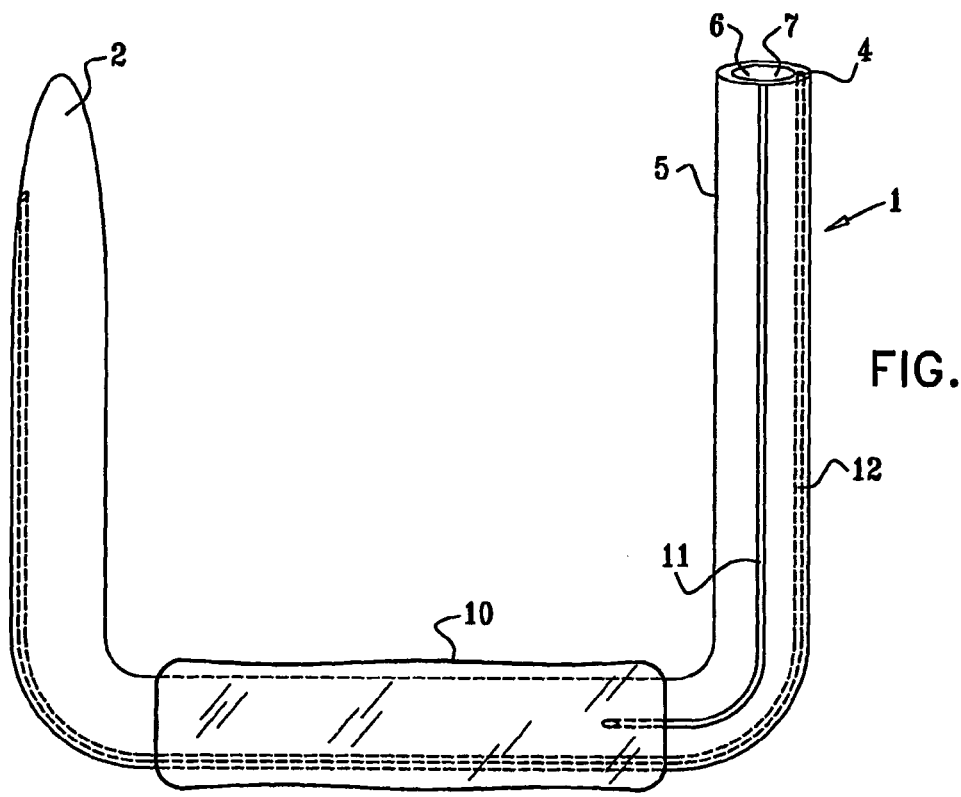
FIG. 1 is a side view of a floating gastrointestinal anchor, in accordance with an embodiment of the present invention.

FIG. 1 depicts floating gastrointestinal anchor 1, in accordance with an embodiment of the present invention. As shown in the embodiment of FIG. 1, anchor 1 has a generally "C" or "U" shape. The anchor has a distal end 2, a proximal end 4, and a side wall 5. The distal end is preferentially tapered for ease of insertion. Proximal end 4 is shaped so as to define an aperture 6 opening into a central core 7, which extends through substantially the entire length of the anchor. The distal end may be either open or closed. The distal end is typically tapered. A rigid insertion rod 8 (described hereinbelow with reference to FIG. 7) is inserted into aperture 6 and central core 7 during insertion of the anchor into the subject. Anchor 1 is made of a material that is flexible enough to be straightened, but has an elastic "memory" to conform to a pre-selected bent shape. The elastic memory may be imparted by the material itself, or alternatively, by the addition of another material. For example, the shape to which the anchor reverts may be determined by the inclusion of an additional material having a memory such as spring steel or a plastic insert. The anchor material comprises a biocompatible material that can withstand the acid environment of the stomach, as is well known to those skilled in the art.

For some applications, located approximately midway between the distal end and the proximal end of the anchor is a balloon 10, which is fixed to and typically surrounds the anchor. Balloon 10 is shown in FIG. 1 in its deflated state. The balloon is typically manufactured of biocompatible material that can withstand the acid environment of the gastric lumen. A conduit channel 11 is typically formed in side wall 5 of the anchor. This conduit channel allows for a thin-walled conduit (not shown) to pass along the side wall of the anchor and into the interior space of balloon 10 for eventual inflation thereof. A guidewire canal 12 is typically formed in the wall of anchor 1 for inserting a guidewire during insertion of the anchor into the stomach. Alternatively, an overtube may be used in lieu of a guidewire during insertion of the anchor into the gastrointestinal tract. If the diameter of the anchor is sufficiently small, a biopsy channel of an endoscope may be used as an overtube to direct the anchor into the gastrointestinal tract.

It is to be noted that balloon 10 may be located with respect to the anchor at the proximal or distal ends or at any site therebetween.

Figure 2:
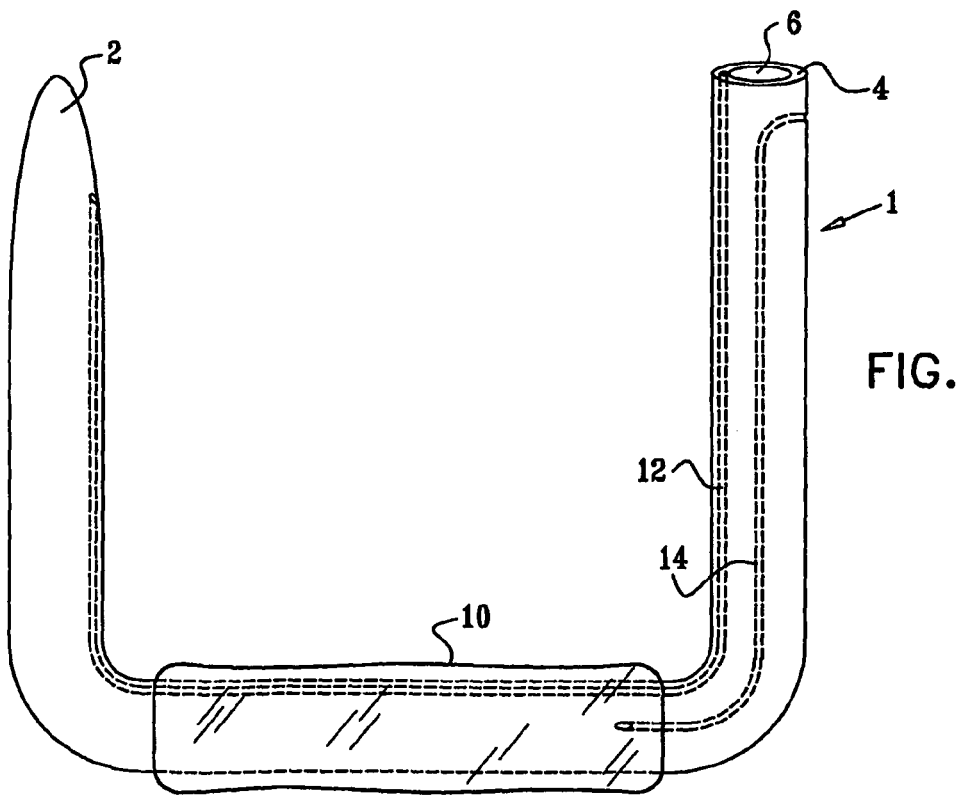

FIGS. 2 and 3 are a side view and a cross-sectional view, respectively, of another configuration of anchor 1 of FIG. 1, in accordance with an embodiment of the present invention. In this configuration, conduit channel 11 of FIG. 1 has been replaced with a conduit canal 14 formed within side wall 5 of anchor 1. For some applications, side wall 5 of the anchor is shaped so as define guidewire canal 12, to allow passage of a guidewire, such as a standard guidewire, e.g., a standard 0.028 inch guidewire, as is well known in the art (as shown in FIG. 3).

FIG. 4 shows anchor 1 of FIG. 2 with a thin-walled conduit 16 inserted into conduit canal 14 of side wall 5 of the anchor and threaded into the interior of balloon 10. (Alternatively, conduit 16 is inserted into conduit channel 11 of side wall 5, as described hereinabove with reference to FIG. 1.) Balloon 10 is shown in its inflated state in FIG. 4. A proximal end 18 of conduit 16 extends a sufficient distance, for example 60 cm, to allow passage of the conduit out of the mouth of the subject while the anchor with the inflated balloon is in the gastric lumen. A fitting 20 is at proximal end 18 of the conduit 16. Fitting 20 typically comprises a "luer-lock" type or equivalent self-sealing mechanism, as is well known to those skilled in the art, for allowing inflation of a balloon in a sealed system. The insertion of the balloon into the stomach promotes a feeling of satiety in the subject and generally interferes with peristaltic waves and gastric emptying. For some applications, conduit 16 is wrapped around an external surface of anchor 1, rather than passed through conduit canal 14 of FIG. 2 or conduit channel 11 of FIG. 1. For these applications, anchor 1 typically is shaped so as to define neither conduit canal 14 nor channel 11.

The caliber of the conduit and its lumen are typically sufficient to allow inflation of any balloon. The conduit comprises a biocompatible material that can withstand the acid environment, and can flex with the anchor in its different conformations. The balloon(s) are inflated to a volume sufficient to fill or partially fill the gastric lumen, which is typically between about 400 and about 1000 cc, depending on stomach size. The anchor typically has external markings from the end of the tapered tip, e.g., every 5 cm, to help guide the operator.

FIG. 5 shows an anchor 22, in accordance with an embodiment of the present invention. Except as described below, anchor 22 is generally similar to anchor 1, described hereinabove with reference to FIGS. 1-4. Anchor 22 is shaped so as to have an "S" configuration, and comprises two or more balloons, e.g., a distal balloon 24 and a proximal balloon 26. For some applications, anchor 22 is shaped so as not to include the portion of the anchor proximal to the proximal balloon. In the multi-balloon configuration shown in FIG. 5, a corresponding number of respective canals are used for guiding conduits into the respective interiors of the balloons. A distal canal 28 guides distal conduit 30 to distal balloon 24, and a proximal canal 32 guides proximal conduit 34 to proximal balloon 26. If more than two balloons are provided, a corresponding number of conduits are used in the same manner. The inflation ports are marked proximal and distal in such a way that is easily recognizable to an endoscopist upon viewing in the gastric lumen.

FIG. 6 shows anchor 22 of FIG. 5 with the proximal and distal balloons in their inflated state.

FIG. 7 is a side view of anchor 1 in a straightened position prior to insertion into the gastrointestinal tract, in accordance with an embodiment of the present invention. Rigid rod 8 is typically extended through the entire length of central core 7 of anchor 1, causing anchor 1 to assume a generally straight configuration. (Alternatively, the rigid rod is extended through only a portion of the length of the central core.) A pushing catheter 36 having a proximal end 37 and a distal end 38 is shown in axial alignment with anchor 1. The pushing catheter 36 has a bore 39 extending entirely therethrough. Rod 8 extends entirely through bore 39 and outside of proximal end 37 of the pushing catheter. Rigid rod 8 typically comprises a rigid unbendable biocompatible material, which easily slips in and out of the pushing catheter. Alternatively, the rigid rod comprises a generally rigid biocompatible material, which, although slightly bendable, is sufficiently rigid to as to easily slip in and out of the pushing catheter. Rigid rod 8 is sufficiently long to fully engage bore 39 of pushing catheter 36, and to extend out of distal end 38 of pushing catheter 36 by between about 35 and about 55 cm, e.g., by approximately 40 cm or approximately 45 cm, for the C-shaped configuration described hereinabove with reference to FIGS. 1-4. The distal portion of rod 8 which extends past distal end 38 of pushing catheter 36 is inserted into central core 7 of anchor 1. When used with other configurations, such as the S-shaped configuration described hereinabove with reference to FIGS. 5 and 6, or the helical configuration described hereinbelow with reference to FIGS. 12A-B, rod 8 has a length appropriate for the length of the core of these configurations.

A pushing tab 40 is preferentially provided in a vicinity of proximal end 37 of the pushing catheter. Tab 40 is used by the endoscopist to push anchor 1 off rod 8, by pushing the tab forward while holding the proximal end of rod 8 stationary with respect to the mouth of the subject. The pushing catheter typically comprises a biocompatible rigid unbendable material, or a generally rigid, but slightly bendable material.

After anchor 1 has been inserted into the gastrointestinal tract and the straightening rod has been removed, the anchor assumes its "C", "S", "U", or any other pre-selected bent shape that the anchor has been configured to assume. By assuming a pre-selected bent shape, the anchor generally prevents migration of the inserted device. The anchor material is flexible enough to enable straightening for deployment, and has a memory shape that remains after rod 8 has been removed. In this way, it facilitates safe atraumatic endoscopic removal, even after having assumed its memory shape. As appropriate, anchor 1 may be partially or completely straightened during removal. Anchor 1 allows carriage of one or more balloons, transmitters, cameras, or any other device that is desired to be placed in the gastric lumen.

Anchor 1, when in the C-configuration described hereinabove with reference to FIGS. 1-4, typically has a total length of between about 30 and about 55 cm, e.g., approximately 40 cm. A central, generally straight, portion typically has a length of between about 15 and about 25 cm, e.g., approximately 16 cm or approximately 20 cm, mid each end portion typically has a length of between about 8 and about 15 cm, e.g., approximately 10 cm or approximately 12 cm. These dimensions may, of course, vary depending on stomach shape and size. Other areas of the gastrointestinal tract require various shapes and sizes. Typically, distal end 2 of anchor 1 is closed and is tapered with a soft flexible tip to allow easy passage through the gastrointestinal tract.

Figure 8:
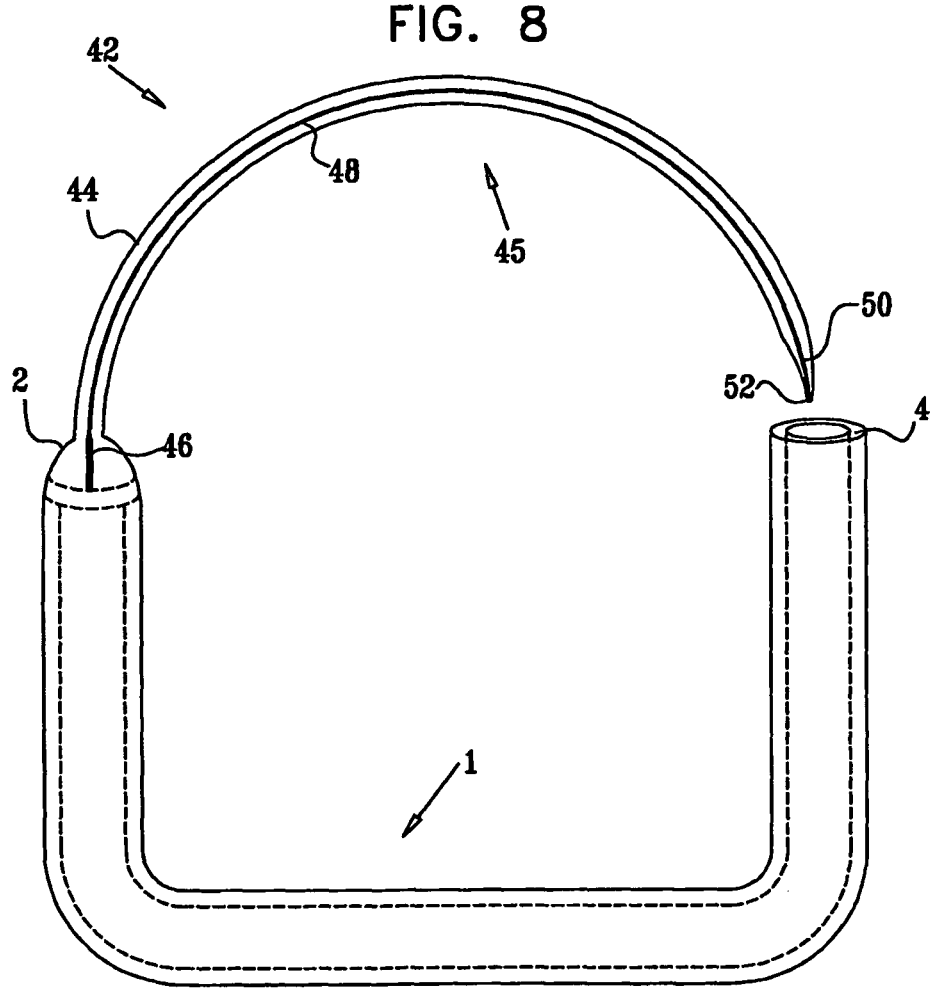
FIG. 8 is an illustration of an appendage attached to the distal end of the anchor of FIG. 1, in accordance with an embodiment of the present invention.

FIG. 8 illustrates an appendage 42 attached to distal end 2 of anchor 1, in accordance with an embodiment of the present invention. Appendage 42 may also be attached to distal end 2 of anchor 22, described hereinabove with reference to FIGS. 5-6 (configuration now shown). Appendage 42 comprises a wire 45 that is housed in a flexible shaft 44. The appendage is preferably an elongated continuation of distal tip 2, comprising the same material as distal tip 2. The appendage is preferably string-like and approximately 3-5 mm in diameter. Wire 45 housed therein is typically a unitary piece, which typically comprises a first relatively short relatively flexible segment 46 (e.g., having a length of approximately 5 cm). As the wire continues within this "string" appendage, a longer relatively stiff segment 48 (e.g., having a length of approximately 8-10 cm) is followed by a third flexible segment 50 (e.g., having a length of approximately 3 cm). Wire 45 alternatively comprises a different arrangement of alternating flexible and stiff segments, each having various lengths.

When balloon 10 is in its deflated state, appendage 42 typically assumes the position shown in FIG. 8, such that a distal end 52 of appendage 42 is positioned in a vicinity of proximal end 4 of anchor 1 (for clarity of illustration, balloon 10 is not shown in FIG. 8; the balloon can be seen in its deflated state in FIG. 1, for example). In this position, appendage 42 provides additional safety for the device when balloon 10 is not inflated. Appendage 42 closes off the gap between proximal end 4 and distal end 2 of anchor 1, thereby preventing any undesired migration out of the stomach and into the pylorus. When balloon 10 is inflated, as shown, for example, in FIG. 4, appendage 42 is easily displaced by the balloon (such that distal end 52 of appendage 42 is no longer positioned in the vicinity of proximal end 4 of anchor 1).

Figure 9:
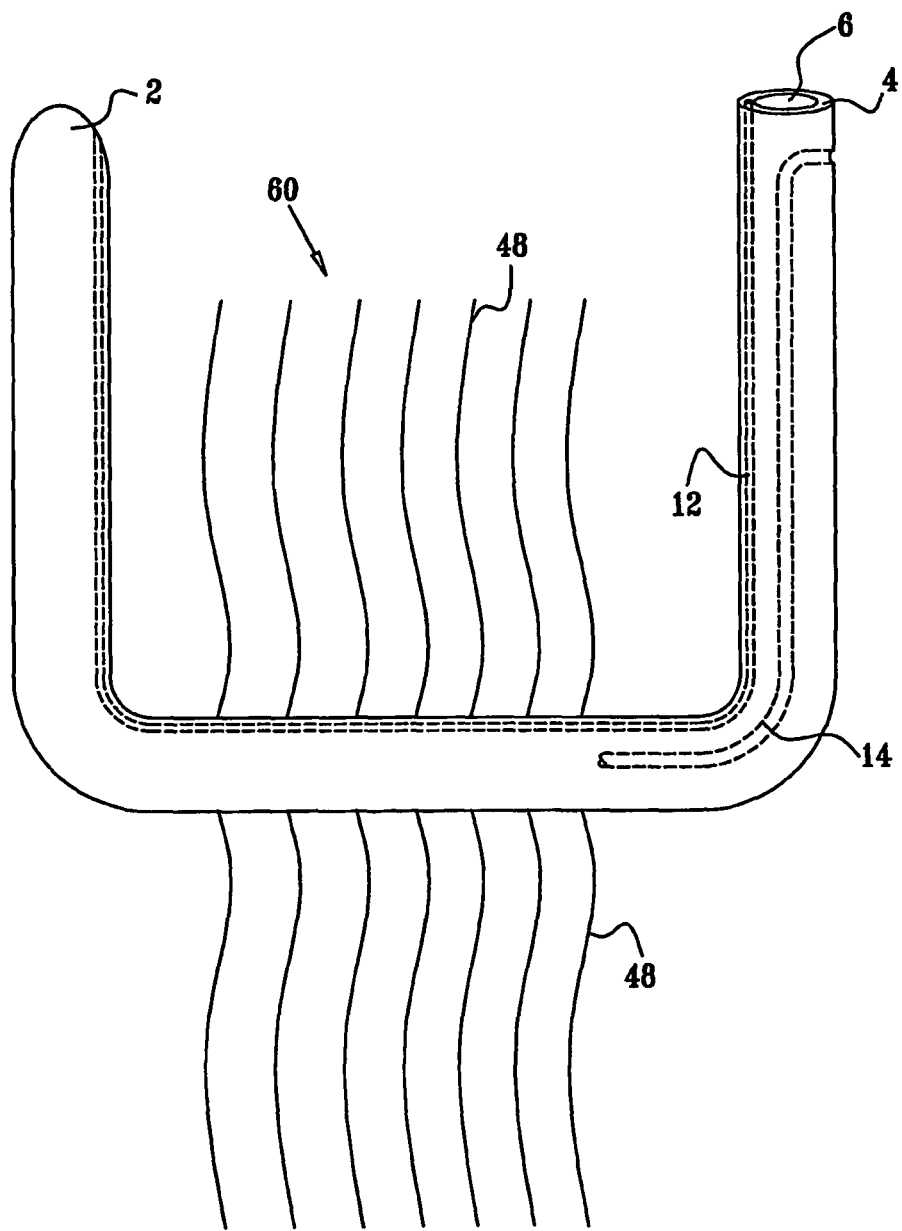
FIGS. 9 and 10 illustrate an attachment coupled to the anchor of FIG. 1, in accordance with respective embodiments of the present invention.
Figure 10:
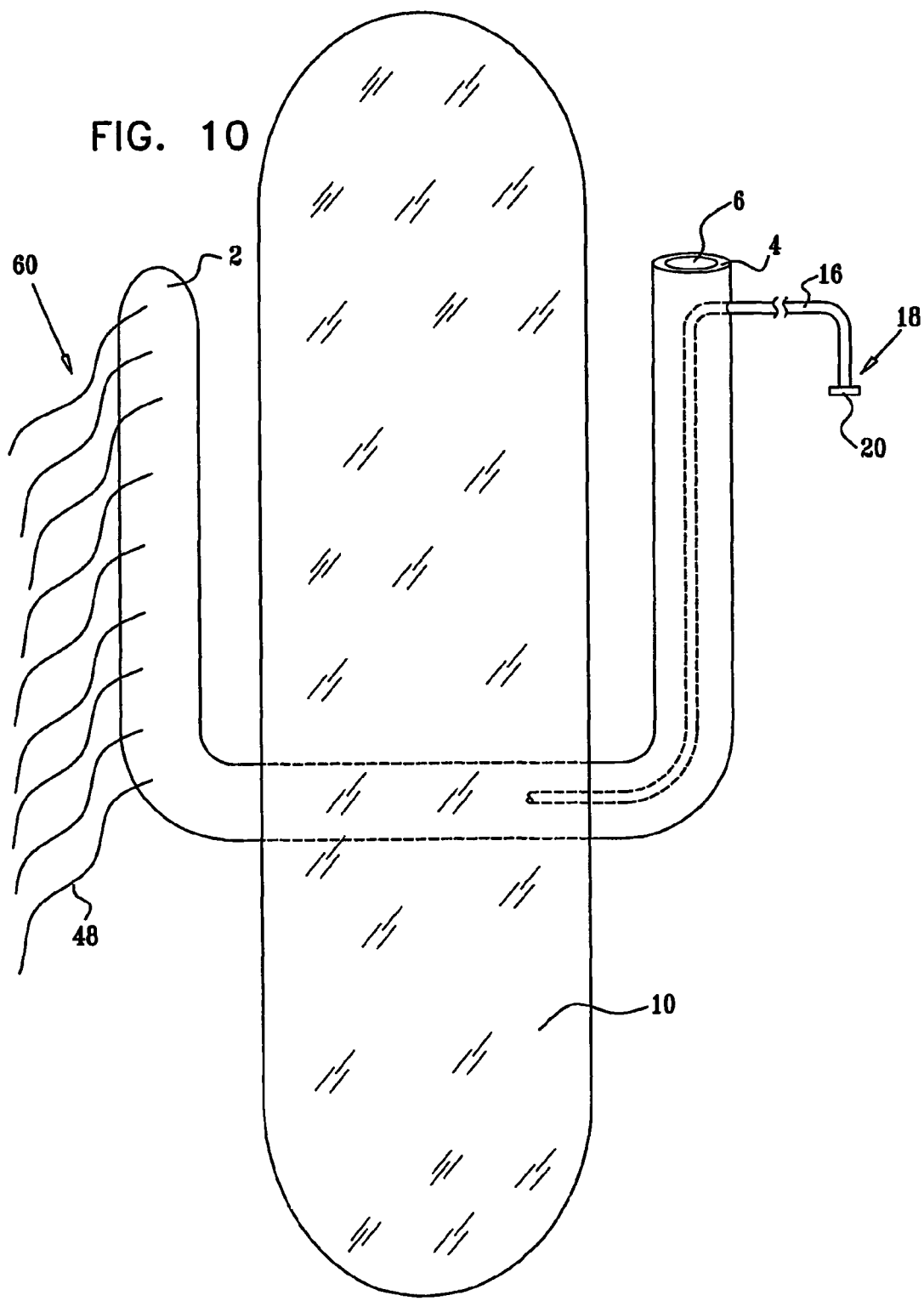

FIGS. 9 and 10 illustrate an attachment 60 coupled to anchor 1, in accordance with respective embodiments of the present invention. Attachment 60 may also be attached to anchor 22, described hereinabove with reference to FIGS. 5-6 (configuration not shown). Attachment 60 comprises one or more elements 48, which may comprise, for example, cord, ribbon, sponges, other thin material, or a combination thereof. Elements 48 typically comprise a biocompatible material. Attachment 60 is adapted to occupy all or a portion of the antrum, thereby interfering with gastric emptying. For some applications, as shown in FIG. 9, attachment 60 is used in lien of balloon 10. In these applications, attachment 60 may be coupled to a central portion of anchor 1, for example. Alternatively, for some applications, as shown in FIG. 10, attachment 60 is used in combination with balloon 10. In these applications, attachment 60 may be coupled to a lateral arm of anchor 1, for example.

Figure 11:
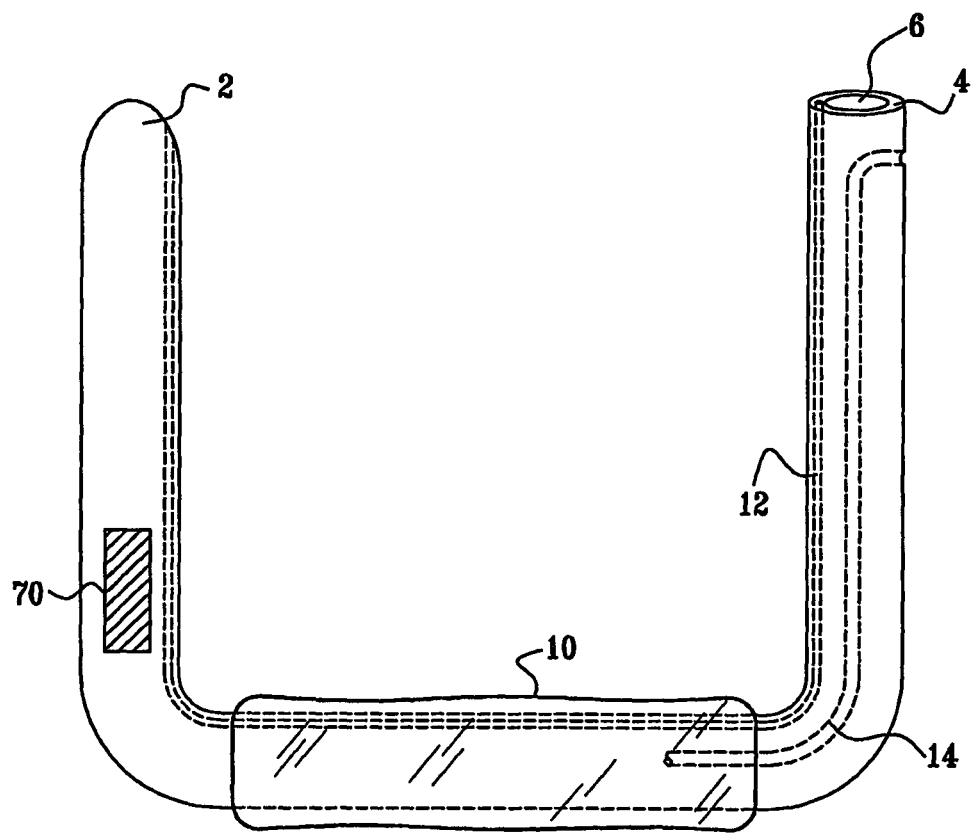
FIG. 11 is a side view of a device and a balloon attached to the anchor of FIG. 1, in accordance with an embodiment of the present invention.

FIG. 11 illustrates a device 70 connected to anchor 1, in accordance with an embodiment of the present invention. Device 70 comprises a transmitting device or any other device, such as a camera which could be placed separately, or in combination with any other device, such as balloon 10 (as shown in FIG. 11). Device 70 may also comprise another type of therapeutic device; for example, device 50 may comprise a device for administering medication or a device for targeting a tumor. For some applications in which device 70 comprises a device for targeting a tumor, device 70 is adapted to administer chemotherapy, radiation therapy, photodynamic therapy, tumor ablation therapy, seed implant therapy, or any other anti-tumor therapy known to those skilled in the art.

Figure 12A:
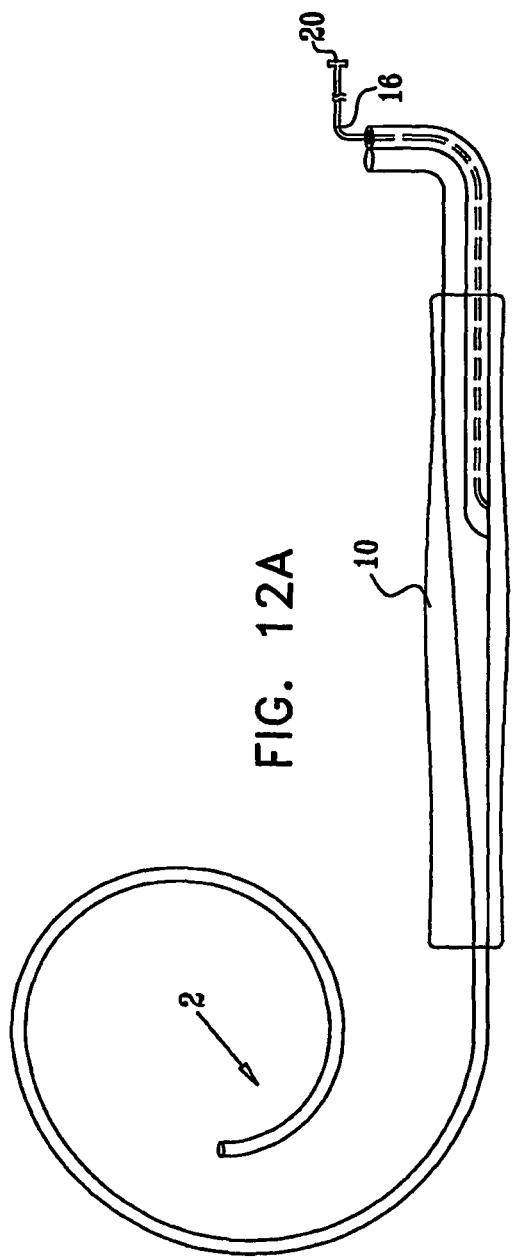
FIG. 12A is a side view of a configuration of the anchor of FIG. 1 in which the anchor has a helically-shaped distal end and a conduit canal within a central core thereof, in accordance with an embodiment of the present invention.
Figure 12B:
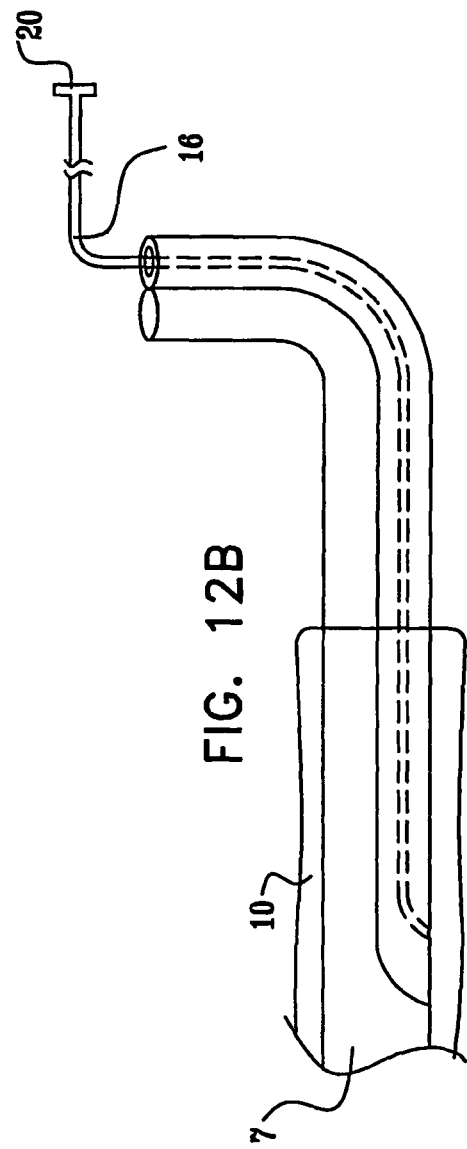
FIG. 12B is an enlarged view of the proximal end of the configuration shown in FIG. 12A, in accordance with an embodiment of the present invention.

Reference is made to FIGS. 12A and 12B, which illustrate a configuration of anchor 1 in which the anchor assumes the bent shape of a helix at its distal end, in accordance with an embodiment of the present invention. For some applications, conduit canal 14 is placed within central core 7. Balloon 10 may be inflated in the conventional manner. The diameter of the helix is typically such that it is not able to pass through the pylorus, for example, between about 4 cm and about 20 cm, e.g., between about 8 cm and about 14 cm. A device is coupled to the straight length of the anchor, such as a therapeutic device, e.g., balloon 10; a transmitting device, e.g., a camera or other transmitting device; or other therapeutic device 70. For some applications, a proximal end of the anchor has a curved tip (e.g., assumes the bent shape of a helix), which generally diminishes tissue trauma by creating an atraumatic surface.

Distal end 2 of the anchors described hereinabove with reference to FIGS. 1-12B is typically not tapered, but rather is rounded to prevent tissue damage upon contact. The anchor typically has an approximately 7-35 Fr caliber, e.g., an approximately 7-20 Fr or an approximately 25-35 Fr caliber. For some applications, an interior surface of the anchor comprises a biocompatible material different from that of the remainder of the anchor, in order to allow passage of rod 8 and/or for shape maintenance. For applications in which separate guidewire canal 12 is not provided, the anchor typically has a smaller caliber, e.g., approximately 6 to 16 Fr. Further alternatively, central core 7 of the anchor is used for a guidewire or for a combination guidewire/straightening rod.

Deployment

It is to be understood that the following examples of use of embodiments of the present invention are not intended to restrict the scope of the present invention.

In an embodiment of the present invention, deployment of the gastrointestinal devices described herein is performed using a gastric overtube or over a guidewire. These standard, well-established techniques are adapted for use with the novel techniques and devices described herein. The guidewire method has been described in the upper gastrointestinal tract with reference to esophageal strictures. For example, techniques may be used that are described in the above-mentioned articles by Kadakia S C et al., Fleischer D E et al., and/or Dumon J R et al., mutatis mutandis, including techniques for esophageal dilators passed over guidewires without the need for fluoroscopy.

In an embodiment of the present invention, the anchors described herein are deployed using the Savary system guidewire technique described by Dumor J R et al., modified as described immediately hereinbelow. Upper endoscopy is performed with complete evaluation of the esophagus stomach and duodenum. The endoscopist measures the distance from the incisors to the gastro-esophageal junction. With the endoscope in the gastric antrum, the guidewire (flexible tip first) is passed under direct vision into the gastric antrum. The guidewire is advanced as the endoscope is removed leaving the guidewire in the gastric lumen. The free end of the guidewire (outside of the mouth) is then placed into the guidewire lumen of the anchor. The anchor is slid down over the guidewire (without changing the position of the guidewire relative to the mouth) and passed into the mouth down the esophagus. When the external markings on the anchor at the incisors are 6-8 cm greater than the level of the gastro-esophageal junction (as noted by the endoscopist during the initial endoscopy), the pushing tab of the pushing catheter is pushed forward while holding the rod stationary relative to the mouth of the subject. Once the anchor is free of the rod, the rod, guidewire, and pushing catheter are removed. The conduit(s) inflation port(s) remain outside of the mouth. The endoscope is then re-inserted to inspect the position of the anchor, and any necessary adjustments are made. The conduit inflation port is then accessed with a luer-lock syringe and inflated with approximately 400-1000 cc of fluid, depending on stomach size, which can be viewed endoscopically. This is repeated for embodiments of the anchor that comprise multiple balloons. The conduit tubing is then pulled down into the stomach using a snare, hook catheter, grabbing forceps, or equivalent. Once the conduit tubing is in the gastric lumen, the endoscope is then removed and the procedure is complete.

If at a later time the balloon(s) need to be adjusted, endoscopy with snare, hook catheter, grabbing forceps, or equivalent access of the free end of the conduit tubing can be performed. The conduit is pulled out of the mouth and inflation or deflation performed, followed by pulling the free end of the conduit into the gastric lumen as described above. As will be evident to those skilled in the art who have read the present application, the embodiments described herein may be placed into the gastrointestinal tract using numerous methods for insertion.

In an embodiment of the present invention, the anchors described herein are deployed using a standard gastric overtube method, modified as described immediately hereinbelow. Standard endoscopy is performed with inspection of the esophagus stomach and duodenum. The endoscope is then removed and a gastric overtube is placed, typically using ordinary techniques. Techniques are typically used that are described in the above-mentioned article by Werth et al., for use of a gastric overtube for foreign body removal and for multiple endoscopic intubations. Once the overtube is in place, the anchor is placed through the overtube. As described hereinabove regarding the guidewire technique, the pushing catheter tab is pushed once the distal tip of the anchor is 6-8 cm beyond the gastro-esophageal junction. When the anchor is off the rod, the rod and pushing catheter are removed. The endoscope can then pass through the overtube and inspect the anchor position, as described hereinabove. The remainder of the procedure is the same as the guidewire procedure described hereinabove.

The anchor, having reverted to its pre-selected bent shape, prevents a deflated balloon from migrating, thereby providing a safe weight loss device. The anchor can be used to anchor more than one balloon, and can anchor any device that needs to remain in the gastric lumen. The anchor can be used in a post-bariatric surgical subject whose weight loss has plateaued and who wishes further weight loss. It can be used anywhere in the gastrointestinal tract where a device of any kind needs to remain in place. The site of the anchor will determine its pre-determined shape, geometry, and size. It is typically placed endoscopically and removed endoscopically under conscious sedation in an outpatient setting.

Reference is now made to FIGS. 13-16, which are schematic illustrations of obesity treatment apparatus 90 comprising a balloon 92 and a floating gastrointestinal anchor 102 coupled thereto, in accordance with an embodiment of the present invention. In general, techniques described hereinabove with respect to other anchors and balloons may be used with apparatus 90, mutatis mutandis.

As is shown in FIG. 13, a highly-stretchable inflation tube 96 protrudes from a first end of balloon 92, typically by a length L2 of about 1-6 cm (e.g., about 2-4 cm). A length L1 of tube 96 of about 6-12 cm (e.g., about 8-9 cm) remains within balloon 92. Tube 96 typically comprises silicone or other stretchable elastomer, or another biocompatible material capable of stretching to at least about 2.5-10 times its original length (e.g., 6 times its original length). Inflation tube 96 is shown in FIG. 13 in an unstretched state, in which an outer diameter D1 thereof is typically about 2-4 mm, e.g., 3 mm. Inflation tube 96 is disposed within a supporting tube 94, which is typically bendable and resilient, and comprises silicone or another suitable material. Support tube 94 is typically fixed to balloon 92 at either end using a sealant 104, which typically comprises a silicone-based or other biocompatible adhesive. An inflation hole 98 in support tube 94, and optionally in inflation tube 96, provides fluid communication between the lumen of balloon 92 and the lumen of tube 96. A closure mechanism 120 typically comprising a luer lock and/or a hand-tightened cap maintains pressure within balloon 92 by preventing fluid leakage therefrom into the subject's stomach.

A rod insertion tube 100 allows insertion of a rigid rod (like rod 8 described hereinabove with reference to FIG. 7) to straighten anchor 102 at the time of implantation of apparatus 90. Once apparatus 90 is located within the subjects stomach, the rigid rod is removed, and anchor 102 assumes an anchoring shape (e.g., the helical shape shown in FIG. 13). Anchor 102 typically but not necessarily remains in the antrum, adjacent to the pyloric valve, and to some extent slows passage of chyme into the duodenum and thereby enhances the sensation of satiety.

Figure 14:
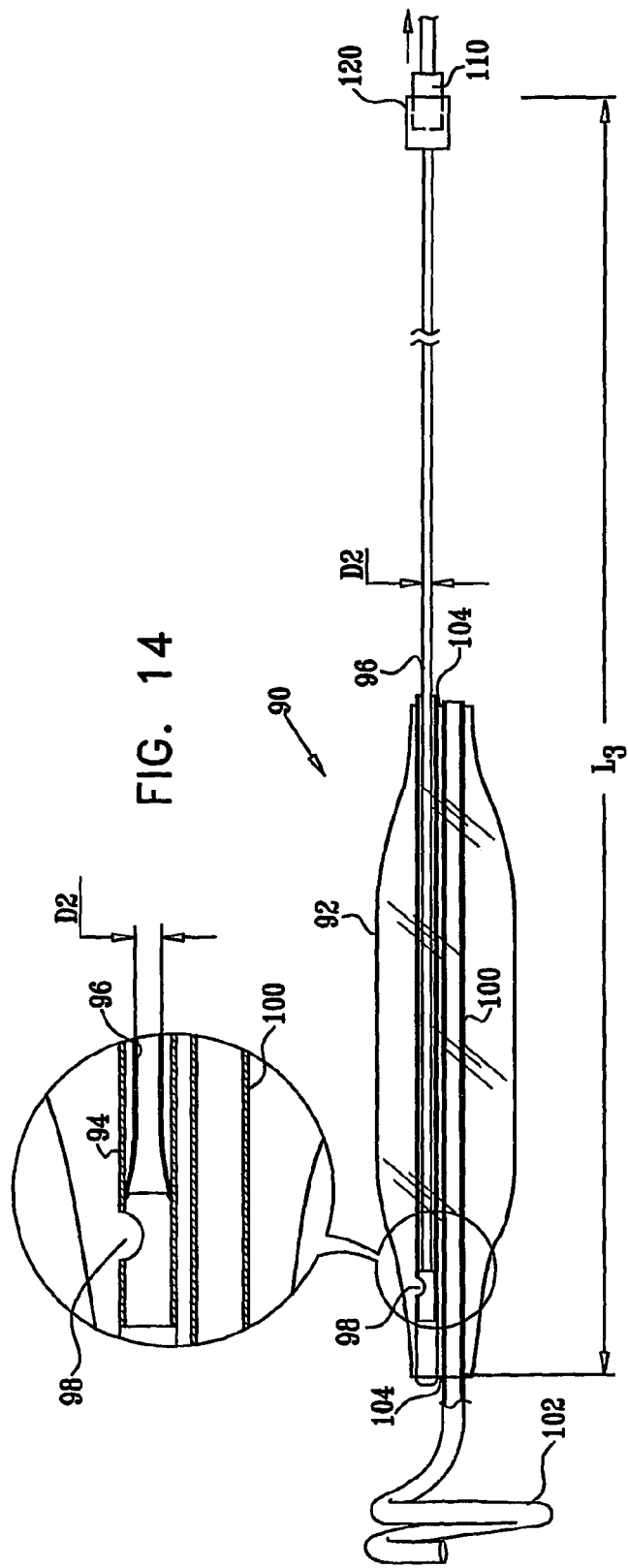
Figure 15:
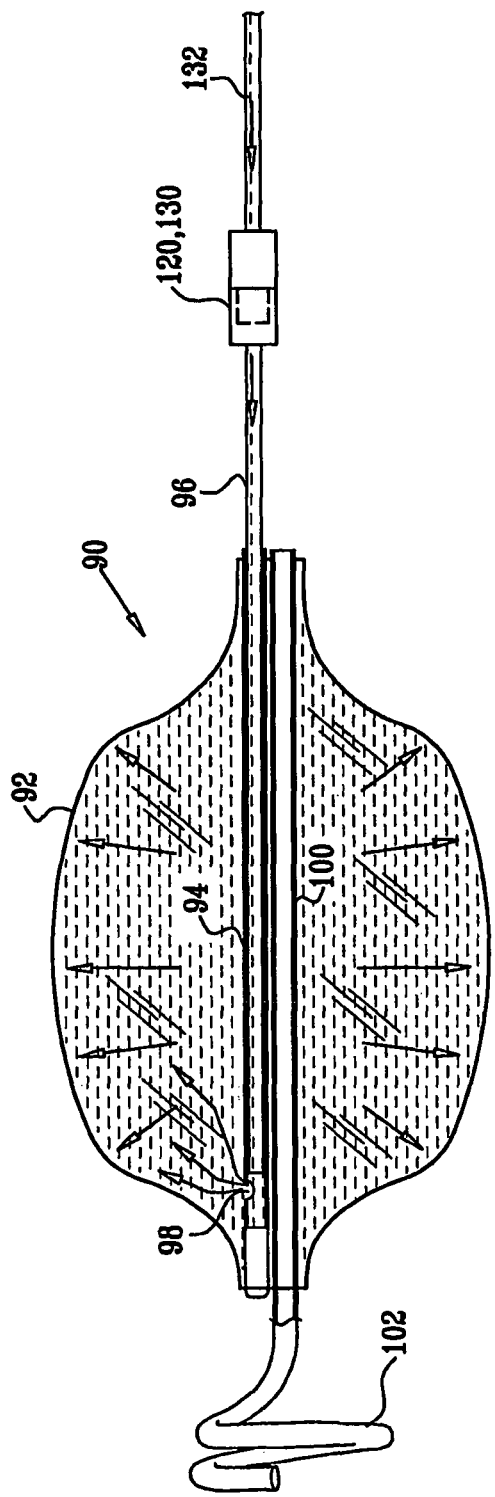
Figure 16:
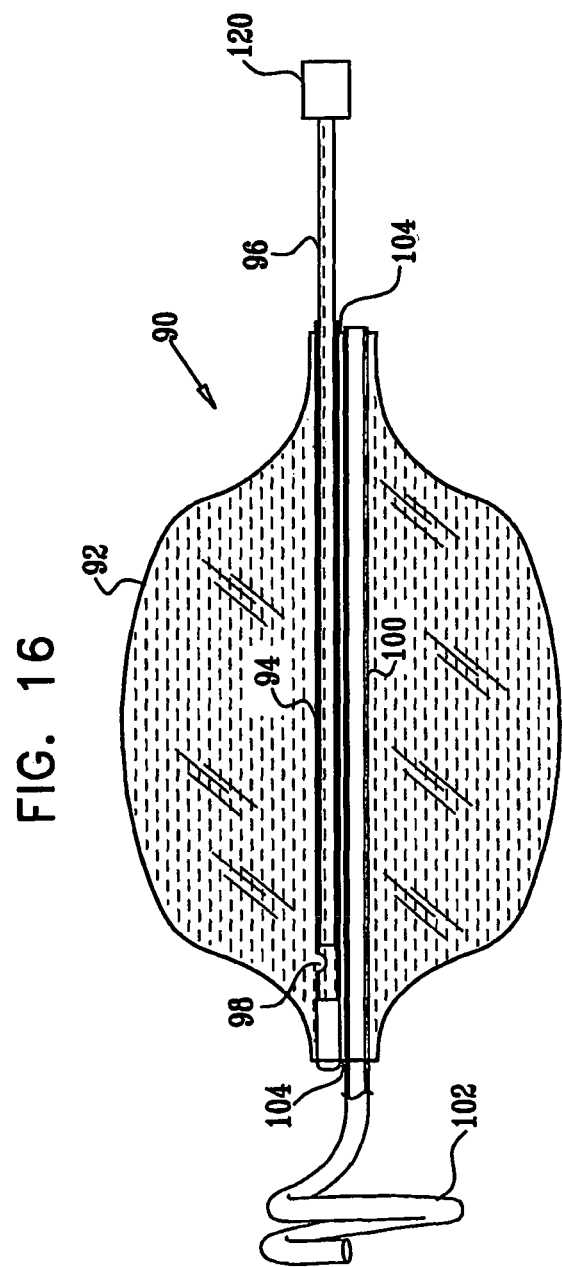

FIG. 13 schematically shows balloon 92 in a partially inflated state, as it may be in the stomach during an initial trial period designed to ascertain whether that level of inflation is sufficient to treat the subject's obesity. If it is determined that the inflation of the balloon is not sufficient, e.g., if the subject is not losing sufficient weight, then balloon 92 is further inflated, as shown in FIGS. 14-16. Similarly, if over the long term the level of inflation of the balloon decreases, then the balloon may be further inflated as shown in FIGS. 14-16.

As shown in FIG. 14, art endoscopic extraction tool 110 couples with closure mechanism 120 or with inflation tube 96, using techniques known in the art, and stretches inflation tube 96 such that it withdraws closure mechanism 120 out of the stomach, through the subject's esophagus, and into (or out of) the subject's mouth. Due to this stretching, the outer diameter of inflation tube 96 decreases to a new diameter D2, smaller than D1. If inflation tube 96 in this stretched state is able to facilitate re-inflation of balloon 92, then closure mechanism 120 is opened while in or just outside of the subject's mouth, and balloon 92 is inflated via inflation tube 96.

Reference is now made to FIG. 15. If it is not practical to inflate balloon 92 while inflation tube 96 is thus stretched, then a temporary filling tube 132 is coupled to closure mechanism 120 or to a temporary coupling valve 130, in order to provide fluid communication between tubes 96 and 132. Inflation tube 96 is gradually returned to the stomach, substantially returning its diameter to D2, and the balloon is inflated by fluid passing through temporary filling tube 132 and inflation tube 96. Subsequently, temporary filling tube 132 is decoupled from inflation tube 96, and closure mechanism 120 is closed, in order to maintain the balloon in its newly inflated state, as shown in FIG. 16.

As appropriate, a similar technique may be used to partially or completely deflate balloon 92.

Reference is now made to FIGS. 17A and 17B, which are schematic illustrations of a bend-limiting tube 140 for placement into gastrointestinal anchor 102 or another anchor, in accordance with all embodiment of the present invention. Bend-limiting tube 140 typically but not necessarily comprises stainless steel, and is shaped to define a plurality of slits 142 which permit tube 140 to assume a straight position, or to bend up to a predefined limit. As appropriate for a given application, the dimensions of slits 142 may differ from those shown in FIGS. 17A and 17B. For example, they could be configured to allow more or less bending of bend-limiting tube 140. Additionally, although slits 142 are shown to be on only one side of bend-limiting tube 140, for some applications the slits are placed in different positions from those shown, so as to, for example, permit limited back and forth flexing of tube 140, or bending in any direction. For example, for applications in which bend-limiting tube 140 is configured for insertion into gastrointestinal anchor 102, slits 142 are placed on tube 140 so as to allow anchor 102 to assume the position shown in FIG. 15, but to inhibit excess curvature of anchor 102 to develop.

For some applications, bend-limiting tube 140 is replaced or supplemented by other bend-limiting tubes for inhibiting excess bending. For example, a series of chained or free beads may be disposed within a bend-limiting tube running along the length of anchor 102, and the close proximity of the beads to each other may be used to limit local bending. As appropriate, the beads may comprise spherical beads or shaped beads with protrusions, so as to limit bending of the anchor. Alternatively or additionally, a bend-limiting tube placed within anchor 102, or running along the length of anchor 102, comprises multiple closely-spaced rings surrounding the bend-limiting tube, whereby excess bending of the bend-limiting tube and the anchor is prevented by contact of the rings.

Figure 18:
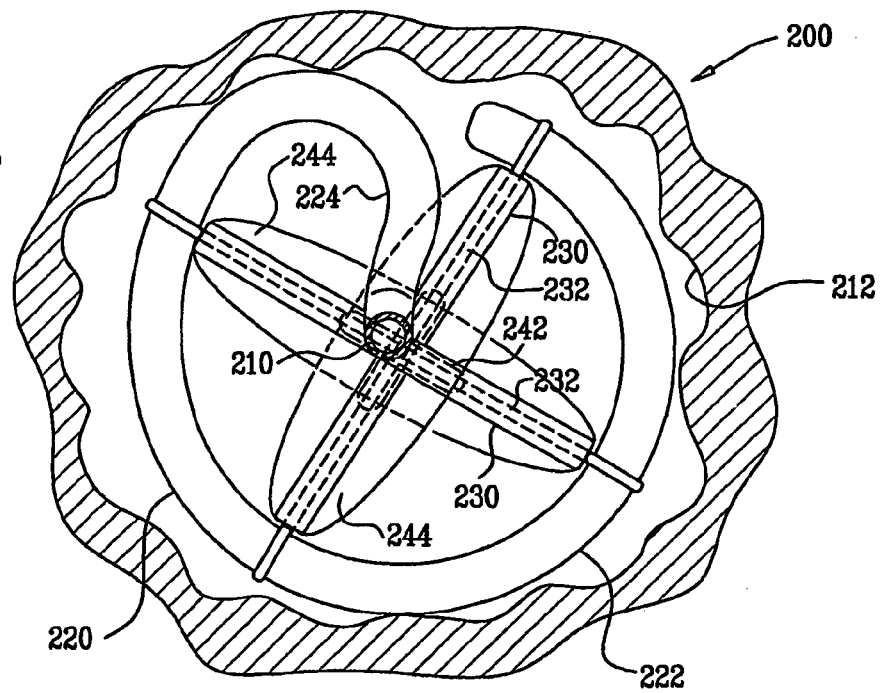
FIG. 18 is a schematic illustration of another floating gastrointestinal anchor, in accordance with an embodiment of the present invention.

Reference is made to FIG. 18, which is a schematic illustration of a floating gastrointestinal anchor 200, in accordance with an embodiment of the present invention. A proximal end 210 of anchor 200 is typically, but not necessarily, coupled to a device, such as a therapeutic device, e.g., a balloon; a transmitting device, e.g., a camera or other transmitting device; or other therapeutic device. For example, proximal end 210 may be coupled to a balloon such as balloon 92, described hereinabove with reference to FIGS. 13-16. Anchor 200 may alternatively or additionally be used in combination with other techniques described hereinabove. Anchor 200 typically, but not necessarily, is positioned in an antrum 212, adjacent to the pyloric valve, and to some extent interferes with natural antral contractions, thereby slowing gastric emptying and enhancing the sensation of satiety.

Anchor 200 comprises a flexible tube 220, which, in its relaxed position, is typically shaped so as to define a generally planar base portion 222, and a proximal portion 224 that projects away from the plane defined by base portion 222, typically in an approximately perpendicular direction. Typically, base portion 222 is generally circular. Alternatively, portion 22 has another shape, such as a rectangle, e.g., a square, or an ellipse. It is noted that the shape described herein and shown in FIG. 18 reflects anchor 200 when it is in its relaxed position. When deployed in the stomach, the shape of the anchor may change because of forces applied thereto by the stomach wall. For some applications, tube 220 comprises silicone, nylon, Pebax® (Arkema), Teflon® (DuPont), stainless steel, nitinol, titanium, or another biocompatible material.

Anchor 200 further comprises at least two cross-bar elements 230, the ends of which are positioned in a vicinity of base portion 222. For applications in which the anchor comprises exactly two cross-bar elements, the two elements are typically approximately perpendicular to one another when the anchor is in its relaxed position, as shown in FIG. 18. The cross-bar elements help maintain the shape of the anchor, so that the anchor interferes with gastric emptying, as mentioned above, and so that the anchor does not pass into a duodenum of the subject. For some applications, cross-bar elements 230 comprise a rigid material, such as metal (e.g., stainless steel), or nylon, Pebax® (Arkema), Teflon® (DuPont), or another similar material, with or without metal inserts, while for other applications the elements comprise a more flexible, but still generally rigid, material, such as plastic or silicone.

Typically, each of cross-bar elements 230 is shaped so as to define a lumen therethrough, and comprises an elastic coupling band 232 that passes through the lumen. Two portions of each of coupling bands 232 protrude from the cross-bar element, and are coupled to base portion 222 at two respective points that are approximately opposite one another. For some applications, bands 232 are generally rigid in central areas thereof, while elastic near the ends thereof. Alternatively, cross-bar elements 230 do not comprise coupling bands 232, and are instead coupled directly to base portion 222. Further alternatively, exactly one end of each cross-bar element is coupled directly to base portion 222.

For some applications, respective central portions 240 of cross-bar elements 230 are shaped so as to define respective cut-outs 242, which better enable the cross-bar elements to occupy approximately the same plane. Alternatively, the central portions are shaped to define indentions that are not cut out. Further alternatively, the cross-bar elements are slightly arced in opposite directions, so as to allow the cross-bar elements to intersect one another while remaining approximately in a single plane. Still further alternatively, the cross-bar elements are shaped like simple cylinders.

Figure 19:
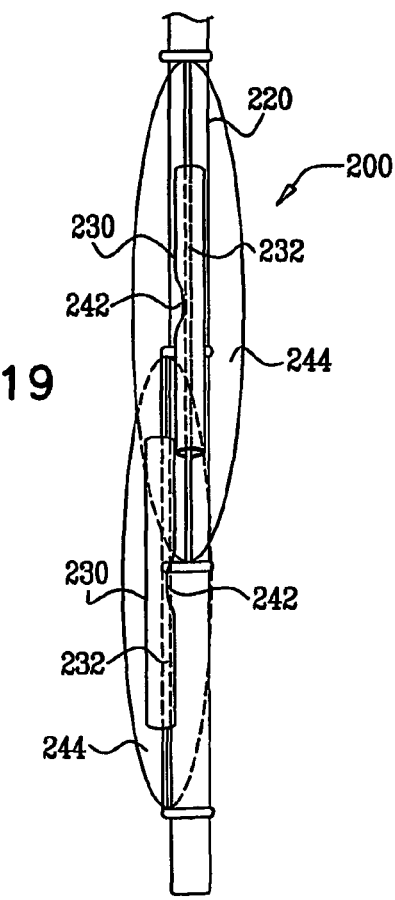
FIG. 19 is a schematic illustration of the anchor of FIG. 18 in a stretched position, in accordance with an embodiment of the present invention.

For some applications, anchor 200 further comprises sleeves 244, each of which encloses a respective cross-bar element 230 and all or a portion of the respective coupling band 232 that protrudes from the cross-bar element. The ends of the sleeves are typically coupled to base portion 222 at the points at which the respective coupling bands are coupled (e.g., as shown in FIG. 19). In this configuration, each sleeve serves as a backup in the event that the respective coupling band 232 fails. Alternatively, sleeves 244 are coupled to the respective bands or to cross-bar elements 230. In either case, sleeves 244 typically help prevent the contents of the stomach from entering cross-bar elements 230. (For the sake of clarity, sleeves 244 are not shown in FIGS. 20A-D, although they may be provided.)

For applications in which base portion 222 is generally circular, the base portion typically has a diameter of between about 5 and about 10 cm, such as about 7 cm, and cross-bar elements 230 have corresponding lengths. Tube 220 of base portion 222 typically has a cross-sectional outer diameter of between about 5 and about 10 mm, such as about 8 mm. The cross-bar elements typically have a cross-sectional outer diameter of between about 4 and about 10 mm, such as about 6 mm. Although many portions of the implantable apparatus described herein have circular cross-sectional shapes, the scope of the present invention include the use of other cross-sectional shapes, as well.

Reference is made to FIG. 19, which is a schematic illustration of anchor 200 in a stretched position, in accordance with an embodiment of the present invention. In order to enable transesophageal insertion of anchor 200 using a gastroscope, the anchor is typically stretched until it assumes an elongated position, in which tube 220 is generally straight. Elastic coupling bands 232 of cross-bar elements 230 enable the anchor to assume this elongated position, in which the cross-bar elements are displaced from their relaxed positions until they are approximately parallel with tube 220. A generally stiff rod is inserted into a lumen of tube 220, in order to maintain the stretched position during insertion (rod not shown in figures). Once the anchor has been partially or completely positioned in the stomach, the rod is removed, allowing the anchor to assume its relaxed position.

Figure 20A:
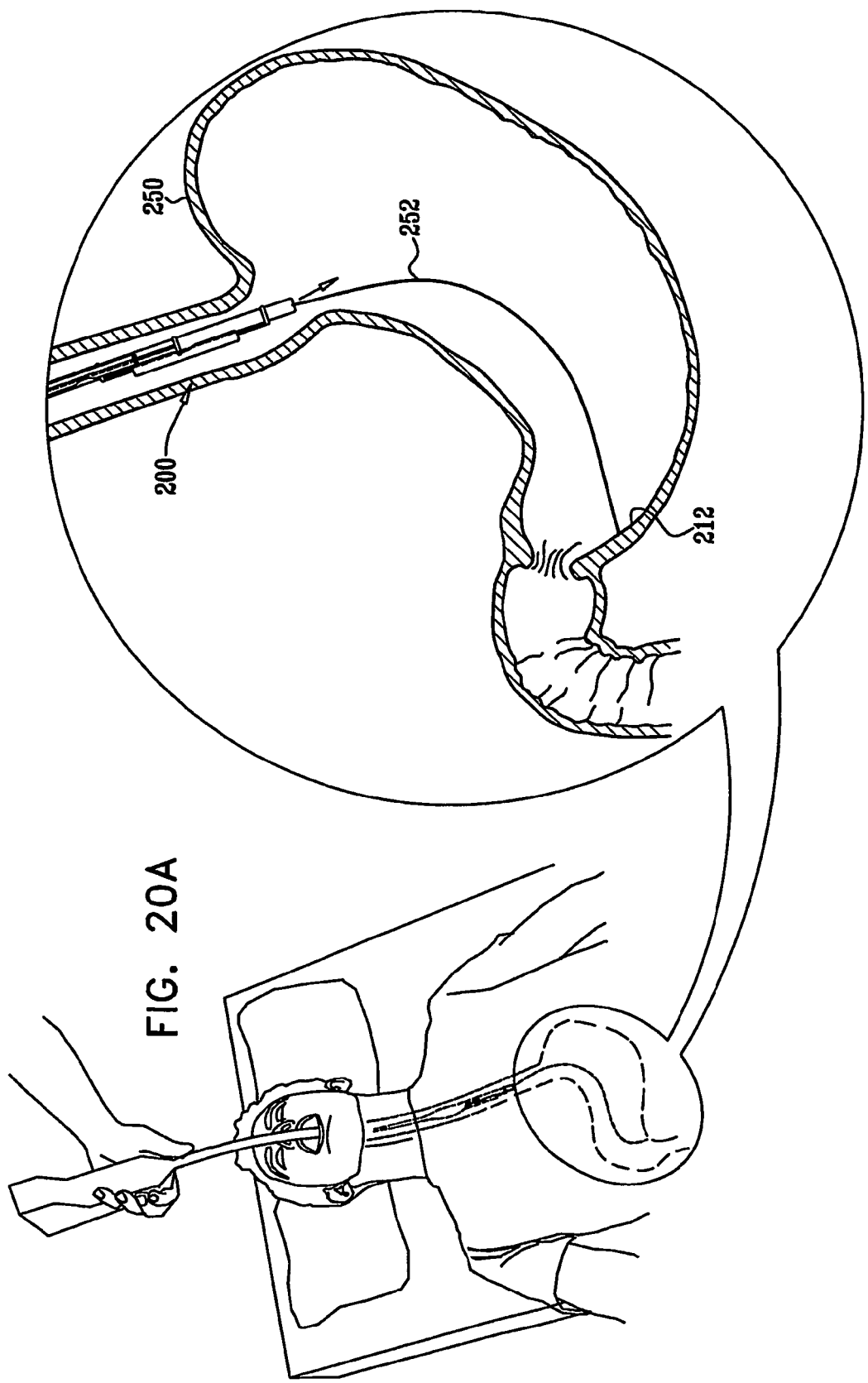

FIGS. 20A-D are schematic illustrations of the deployment of anchor 200, in accordance with an embodiment of the present invention. Prior to insertion of anchor 200 into the subject, a guidewire 252 is transesophageally inserted into a stomach 250, such as using an gastroscope, as is known in the art. The distal end of the guidewire is maneuvered to antrum 212, and the gastroscope is removed from the subject. (Insertion of guidewire 252 is not shown in the figures.) Anchor 200 is configured to assume its elongated position, by inserting the generally stiff rod into the lumen of tube 220, as described hereinabove with reference to FIG. 19. As shown in FIG. 20A, the elongated anchor is transesophageally inserted into stomach 250 over guidewire 252, which passes through a lumen of the elongating rod.

Figure 20B:
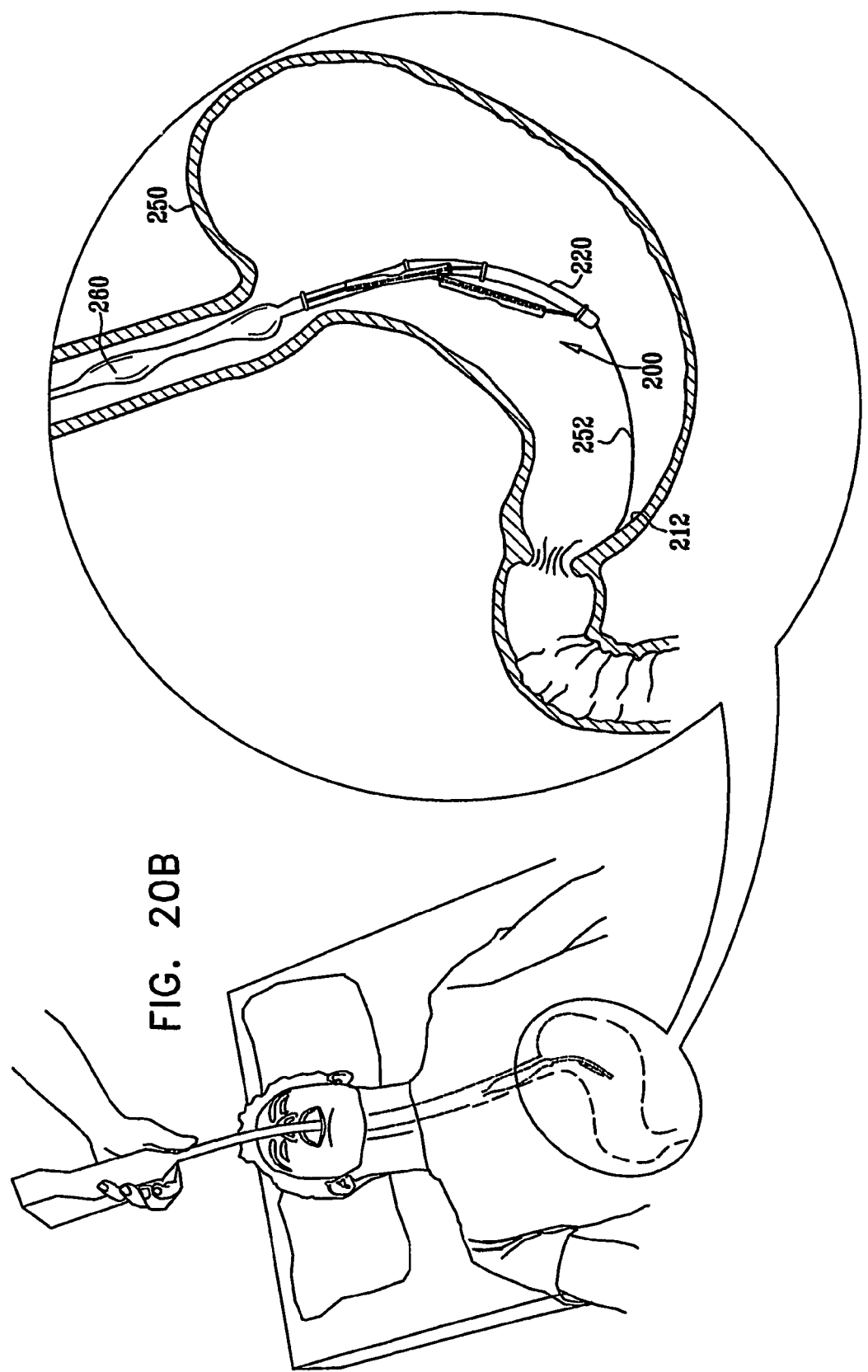
Figure 20C:
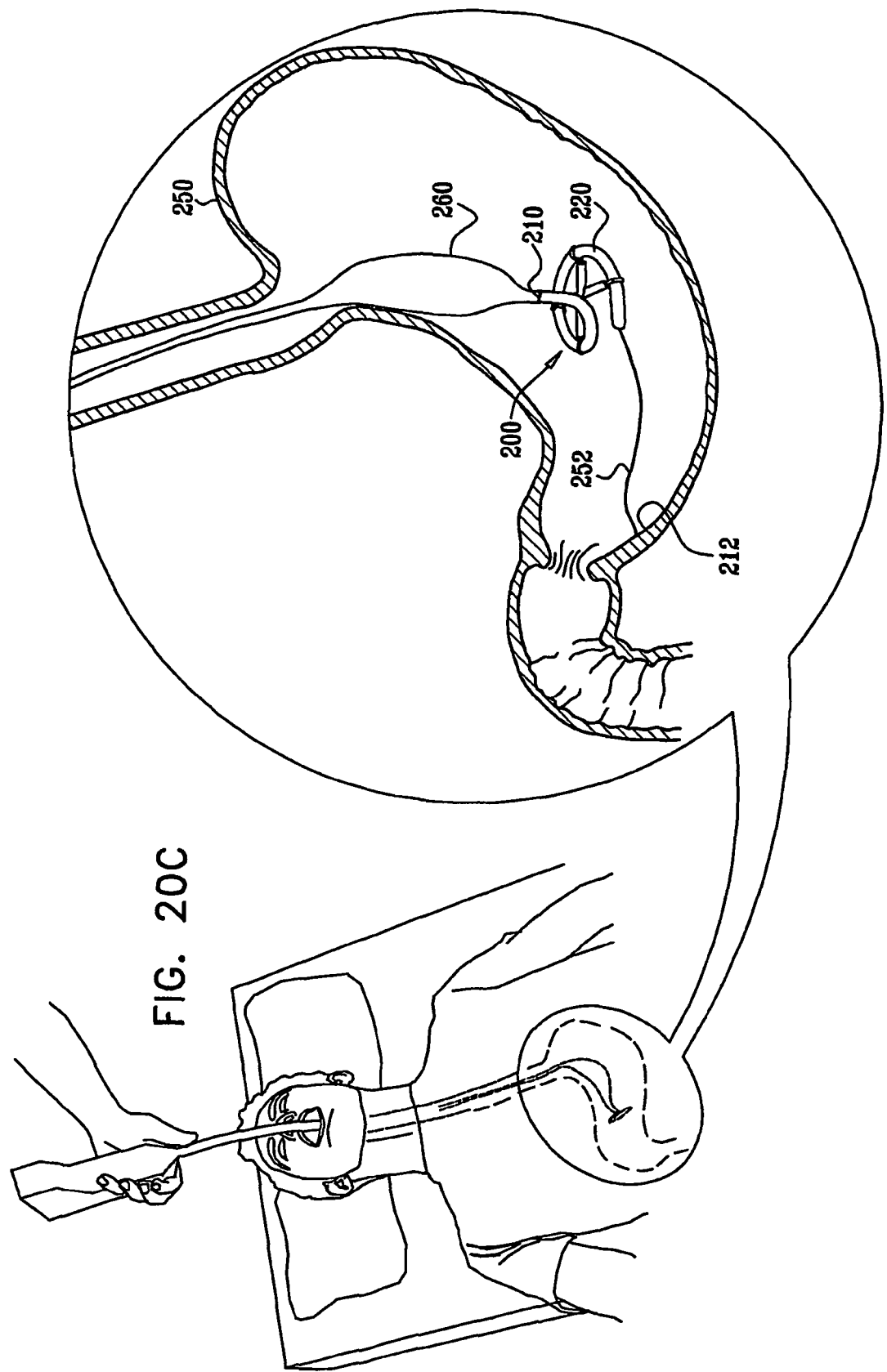

As shown in FIGS. 20B-C, once in stomach 250, anchor 200 is allowed to gradually return to its relaxed position, by withdrawal of the rod. Withdrawal of the rod typically includes pushing a portion of the implantable apparatus (e.g., balloon 260 or anchor 200) off of the rod. For some applications, a distal tip of a pushing tool (not shown) is coupled to the portion of the implantable apparatus such that, if desired, the pushing tool can also at least partially pull the portion of the implantable apparatus back onto the rod. For these applications, the pushing tool typically grasps or is otherwise releasably coupled to the portion of the implantable apparatus, and can be released by the physician from the portion when the rod is sufficiently withdrawn. Anchor 200 is shown partially relaxed in FIG. 20B, and fully relaxed in FIG. 20C. It is noted that the withdrawal of the elongating rod typically begins as soon as possible during the insertion procedure (and prior to the anchor reaching the antrum), in order to minimize the likelihood of the rod applying undue forces to the stomach. In the embodiment shown in FIG. 20C, anchor 200 is coupled to a balloon 260, such as balloon 92, described hereinabove with reference to FIGS. 13-16. In FIG. 20D, balloon 260 has been fully inflated, anchor 200 is positioned in antrum 212, and guidewire 252 is withdrawn from the subject. Typically, a gastroscope is used for visually confirming proper placement and deployment of the anchor and/or inflation of balloon 260.

The scope of the present invention includes the use of any of the anchors described hereinabove without simultaneous use of a balloon. In these embodiments, the anchor typically slows gastric emptying and/or fills space and thereby induces a sensation of satiety. As appropriate, generally helical anchors described hereinabove and shown in the figures may include more turns, for example so as to occupy half of the stomach or even substantially all of the stomach (instead of just the portion near the antrum, as shown in some of the figures).

Embodiments described herein may be practiced in combination with techniques described in one or more of the following applications, which are assigned to the assignee of the present patent application and are incorporated herein by reference: U.S. patent application Ser. No. 11/132,855, filed May 18, 2005; U.S. Provisional Patent Application 60/639,843, filed Dec. 27, 2004; PCT Patent Application PCT/IL2005/001381, filed Dec. 27, 2005; U.S. Provisional Patent application 60/787,124 filed by Brooks on Mar. 28, 2006, entitled, "Floating gastrointestinal anchor"; and U.S. Provisional Patent application 60/815,624 filed by Brooks on Jun. 20, 2006, entitled, "Floating gastrointestinal anchor." The scope of the present invention includes embodiments described in each of these five applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use in a stomach of a subject, the apparatus comprising:
   a balloon, adapted for placement in the stomach;
   an anchor, coupled to the balloon and adapted to prevent the balloon from passing into a duodenum of the subject;
   an inflation tube, which is (a) coupled to the balloon to permit inflation of the balloon, (b) elastically stretchable from a resting length thereof to a longer, stretched length, and (c) adapted to be elastically stretched from the stomach to a mouth of the subject to facilitate inflation of the balloon; and
   a filling tube configured to be temporarily coupled to the inflation tube while the inflation tube is elastically stretched, and configured to facilitate inflation of the balloon when the inflation tube is relaxed at least in part following being elastically stretched.

2. The apparatus according to claim 1, wherein the inflation tube is adapted to be elastically stretchable to more than 2.5 times the resting length thereof.

3. The apparatus according to claim 1, wherein the anchor is configured to be positioned in an antrum of the stomach such that the anchor interferes at least to some extent with natural antral contractions of the antrum.

4. The apparatus according to claim 1, wherein the balloon is adapted to promote a feeling of satiety in the subject.

5. The apparatus according to claim 1, wherein the balloon is adapted to interfere with peristaltic waves and gastric emptying of the subject.

6. The apparatus according to claim 1, comprising a device coupled to the anchor, selected from the list consisting of a therapeutic device, and a transmitting device.

7. The apparatus according to claim 1, comprising a closure mechanism coupled to a proximal end of the inflation tube, configured to maintain pressure within the balloon by preventing leakage of fluid therefrom into the stomach of the subject.

8. The apparatus according to claim 1, comprising an extraction tool configured to elastically stretch the inflation tube by reversibly engaging the inflation tube and, while the extraction tool is coupled to the inflation tube, pulling on the inflation tube.

9. The apparatus according to claim 1, wherein the inflation tube is adapted to return to the stomach following elastic stretching from the stomach to the mouth.

10. The apparatus according to claim 1, wherein the inflation tube has a length of between 7 and 18 cm in an unstretched state of the inflation tube.

11. The apparatus according to claim 1, wherein the inflation tube is configured to return to the resting length when no longer stretched.

12. The apparatus according to claim 1, wherein the inflation tube has a first outer diameter when at the resting length and a second outer diameter when at the longer stretched length, and wherein the second outer diameter is smaller than the first outer diameter.

13. Apparatus for use in a stomach of a subject, the apparatus comprising:
 a balloon, adapted for placement in the stomach;
 an anchor, coupled to the balloon and adapted to prevent the balloon from passing into a duodenum of the subject, the anchor comprising a resilient tube;
 an inflation tube, which is (a) coupled to the balloon to permit inflation of the balloon, (b) elastically stretchable from a resting length thereof to a longer, stretched length, and (c) adapted to be elastically stretched from the stomach to a mouth of the subject to facilitate inflation of the balloon; and
 a bend-limiting tube coupled to the resilient tube, the bend-limiting tube configured to limit an extent of bending of the resilient tube.

14. The apparatus according to claim 13, wherein the inflation tube is configured to be disposed within the resilient tube, the resilient tube permitting the inflation tube to assume a straight position, or to bend up to a predefined limit.

15. The apparatus according to claim 13, wherein the inflation tube is adapted to be elastically stretchable to more than 2.5 times the resting length thereof.

16. The apparatus according to claim 13, comprising a closure mechanism coupled to a proximal end of the inflation tube, configured to maintain pressure within the balloon by preventing leakage of fluid therefrom into the stomach of the subject.

17. The apparatus according to claim 13, comprising an extraction tool configured to elastically stretch the inflation tube by reversibly engaging the inflation tube and, while the extraction tool is coupled to the inflation tube, pulling on the inflation tube.

18. The apparatus according to claim 13, wherein the inflation tube is adapted to return to the stomach following elastically stretching from the stomach to the mouth.

19. The apparatus according to claim 13, wherein the inflation tube has a length of between 7 and 18 cm in an unstretched state of the inflation tube.

20. The apparatus according to claim 13, wherein the inflation tube has a first outer diameter when at the resting length and a second outer diameter when at the longer stretched length, and wherein the second outer diameter is smaller than the first outer diameter.

21. Apparatus for use in a stomach of a subject, the apparatus comprising:
 a balloon, adapted for placement in the stomach;
 an anchor, coupled to the balloon and adapted to prevent the balloon from passing into a duodenum of the subject, the anchor comprising a material that has an elastic memory which biases the anchor towards assuming a pre-selected bent configuration;
 an inflation tube, which is (a) coupled to the balloon to permit inflation of the balloon, (b) elastically stretchable from a resting length thereof to a longer, stretched length, and (c) adapted to be elastically stretched from the stomach to a mouth of the subject to facilitate inflation of the balloon; and
 a straightening rod, and wherein:
  the anchor has a distal end and an open proximal end;
  the anchor is shaped so as to define a central core extending from the open proximal end toward the distal end; and
  the anchor is configured to be straightened from the pre-selected bent configuration by insertion of the straightening rod in the central core.

22. The apparatus according to claim 21, wherein the inflation tube is adapted to be elastically stretchable to more than 2.5 times the resting length thereof.

23. The apparatus according to claim 21, comprising a closure mechanism coupled to a proximal end of the inflation tube, configured to maintain pressure within the balloon by preventing leakage of fluid therefrom into the stomach of the subject.

24. The apparatus according to claim 21, comprising an extraction tool configured to elastically stretch the inflation tube by reversibly engaging the inflation tube and, while the extraction tool is coupled to the inflation tube, pulling on the inflation tube.

25. The apparatus according to claim 21, wherein the inflation tube is adapted to return to the stomach following elastically stretching from the stomach to the mouth.

26. The apparatus according to claim 21, wherein the inflation tube has a length of between 7 and 18 cm in an unstretched state of the inflation tube.

27. The apparatus according to claim 21, wherein the inflation tube has a first outer diameter when at the resting length and a second outer diameter when at the longer stretched length, and wherein the second outer diameter is smaller than the first outer diameter.

28. A method, comprising:
 inserting into a stomach of a subject a gastric balloon in fluid communication with an inflation tube, such that a closure mechanism at a proximal end of the inflation tube is within the stomach;
 assessing an inflation level of the balloon following insertion thereof;
 in response to identifying a need for inflation of the balloon, elastically stretching the inflation tube while keeping the balloon within the stomach, so as to withdraw the closure mechanism out of the stomach and through an esophagus of the subject; and
 following the elastic stretching of the inflation tube, inflating the balloon via the inflation tube.

29. The method according to claim 28, wherein assessing the inflation level of the balloon comprises determining a level of weight loss of the subject and correlating weight loss to the level of inflation of the balloon.

30. The method according to claim 28, wherein inflating the balloon comprises injecting a fluid into the inflation tube while the proximal end of the inflation tube is outside of a body of the subject.

31. The method according to claim 28, comprising temporarily coupling the inflation tube to a filling tube following the stretching of the inflation tube, and wherein inflating the balloon comprises:
- allowing at least a portion of the inflation tube to return to the stomach while the filling tube is coupled to the inflation tube; and
- injecting a fluid into the inflation tube via the filling tube while the portion of the inflation tube remains disposed within the stomach.

32. The method according to claim 28, wherein stretching the inflation tube comprises extracting the proximal end of the inflation tube from a mouth of the subject.

33. The method according to claim 32, wherein extracting the proximal end of the inflation tube comprises elastically stretching the inflation tube to at least 2.5 times a resting length thereof.

34. The method according to claim 28, further comprising allowing return of the inflation tube to the stomach following the stretching.

35. The method according to claim 28, wherein stretching the inflation tube comprises using an extraction tool to reversibly engage the inflation tube and pull on the inflation tube while the extraction tool is coupled to the inflation tube.

36. The method according to claim 28, wherein the inflation tube has a first outer diameter when at a resting length, and wherein the elastically stretching the inflation tube comprises decreasing an outer diameter of the inflation tube to a second outer diameter smaller than the first outer diameter.

37. Apparatus for use in a stomach of a subject, the apparatus comprising:
- a balloon, adapted for placement in the stomach;
- an anchor, coupled to the balloon and adapted to prevent the balloon from passing into a duodenum of the subject;
- an inflation tube, which is (a) coupled to the balloon to permit inflation of the balloon, (b) elastically stretchable from a resting length thereof to a longer, stretched length, and (c) adapted to be elastically stretched from the stomach to a mouth of the subject to facilitate inflation of the balloon; and
- a supporting tube that is fixed within the balloon, wherein the elastically stretchable inflation tube is positioned partially within the supporting tube.

38. The apparatus according to claim 37, wherein the inflation tube is adapted to be elastically stretchable to more than 2.5 times the resting length thereof.

39. The apparatus according to claim 37, comprising a closure mechanism coupled to a proximal end of the inflation tube, configured to maintain pressure within the balloon by preventing leakage of fluid therefrom into the stomach of the subject.

40. The apparatus according to claim 37, comprising an extraction tool configured to elastically stretch the inflation tube by reversibly engaging the inflation tube and, while the extraction tool is coupled to the inflation tube, pulling on the inflation tube.

41. The apparatus according to claim 37, wherein the inflation tube is adapted to return to the stomach following elastically stretching from the stomach to the mouth.

42. The apparatus according to claim 37, wherein the inflation tube has a length of between 7 and 18 cm in an unstretched state of the inflation tube.

43. The apparatus according to claim 37, wherein the inflation tube has a first outer diameter when at the resting length and a second outer diameter when at the longer stretched length, and wherein the second outer diameter is smaller than the first outer diameter.

44. Apparatus for use in a stomach of a subject, the apparatus comprising:
- a balloon, adapted for placement in the stomach; and
- an inflation tube, which is
    (a) coupled to the balloon to permit inflation of the balloon,
    (b) elastically stretchable from a resting length thereof to a longer, stretched length, and
    (c) adapted to be elastically stretched from the stomach to a mouth of the subject to facilitate inflation of the balloon.

45. The apparatus according to claim 44, wherein the inflation tube is adapted to be elastically stretchable to more than 2.5 times the resting length thereof.

46. The apparatus according to claim 44, comprising a closure mechanism coupled to a proximal end of the inflation tube, configured to maintain pressure within the balloon by preventing leakage of fluid therefrom into the stomach of the subject.

47. The apparatus according to claim 44, comprising an extraction tool configured to elastically stretch the inflation tube by reversibly engaging the inflation tube and, while the extraction tool is coupled to the inflation tube, pulling on the inflation tube.

48. The apparatus according to claim 44, wherein the inflation tube is adapted to return to the stomach following elastically stretching from the stomach to the mouth.

49. The apparatus according to claim 44, wherein the resting length of the inflation tube is between 7 and 18 cm.

50. The apparatus according to claim 44, wherein the inflation tube has a first outer diameter when at the resting length and a second outer diameter when at the longer stretched length, and wherein the second outer diameter is smaller than the first outer diameter.

* * * * *